(12) United States Patent
Dong et al.

(10) Patent No.: US 10,077,228 B2
(45) Date of Patent: Sep. 18, 2018

(54) FERROCENE-BASED COMPOUNDS AND PALLADIUM CATALYSTS BASED THEREON FOR THE ALKOXYCARBONYLATION OF ETHYLENICALLY UNSATURATED COMPOUNDS

(71) Applicant: EVONIK DEGUSSA GMBH, Essen (DE)

(72) Inventors: Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Robert Franke, Marl (DE); Dieter Hess, Marl (DE); Katrin Marie Dyballa, Recklinghausen (DE); Dirk Fridag, Haltern am See (DE); Frank Geilen, Haltern am See (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/213,456

(22) Filed: Jul. 19, 2016

(65) Prior Publication Data
US 2017/0022236 A1   Jan. 26, 2017

(30) Foreign Application Priority Data
Jul. 23, 2015 (DE) .................. 10 2015 213 918

(51) Int. Cl.
*C07C 67/38* (2006.01)
*C07F 9/58* (2006.01)
(Continued)

(52) U.S. Cl.
CPC ........... *C07C 67/38* (2013.01); *B01J 31/2295* (2013.01); *B01J 31/24* (2013.01); *B01J 31/2404* (2013.01);
(Continued)

(58) Field of Classification Search
CPC ......... C07C 67/38; C07F 9/587; C07F 9/5726
(Continued)

(56) References Cited

U.S. PATENT DOCUMENTS 5,679,831 A  10/1997 Sielcken
6,433,242 B1  8/2002 Wiese
(Continued)

FOREIGN PATENT DOCUMENTS

CN     102531890 A    7/2012
DE  10 2008 007081 A1  8/2009
(Continued)

OTHER PUBLICATIONS

Nifant'ev, I. E., et al., Metallocenephosphoramides, 2.* Amides of Ferrocenephosphonous and Ferrocenediphosphonous Acids, Phosphorus, Sulfur, and Silicon and the Related Elements, 1992, vol. 68, pp. 99-106. (8 pages).
(Continued)

*Primary Examiner* — D Margaret M Seaman
(74) *Attorney, Agent, or Firm* — Smith, Gambrell & Russell, LLP

(57) ABSTRACT

The invention relates to a compound of formula (I)

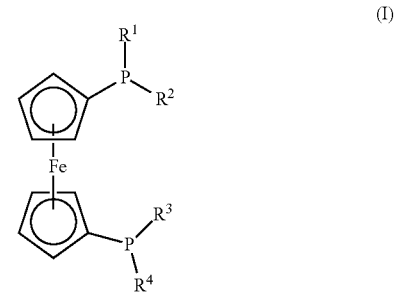

(I)

where
$R^1$, $R^2$, $R^3$, $R^4$ are each independently selected from —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl;
at least one of the $R^1$, $R^2$, $R^3$, $R^4$ radicals is a —$(C_6-C_{20})$-heteroaryl radical having at least six ring atoms;
and
$R^1$, $R^2$, $R^3$, $R^4$, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—[$(C_1-C_{12})$-alkyl]$_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

The invention further relates to precursors for preparation of the compound according to the invention, to Pd complexes comprising the compound according to the invention and to the use thereof in alkoxycarbonylation.

16 Claims, 6 Drawing Sheets

(51) Int. Cl.
| | |
|---|---|
| *C07F 9/6506* | (2006.01) |
| *C07F 15/00* | (2006.01) |
| *B01J 31/24* | (2006.01) |
| *B01J 31/22* | (2006.01) |
| *C07F 9/572* | (2006.01) |
| *C07F 9/655* | (2006.01) |
| *C07F 9/6553* | (2006.01) |
| *C07F 17/02* | (2006.01) |

(52) U.S. Cl.
CPC ......... *B01J 31/2409* (2013.01); *C07F 9/5726* (2013.01); *C07F 9/587* (2013.01); *C07F 9/65066* (2013.01); *C07F 9/65515* (2013.01); *C07F 9/655345* (2013.01); *C07F 15/006* (2013.01); *C07F 17/02* (2013.01); *B01J 2231/321* (2013.01); *B01J 2231/49* (2013.01); *B01J 2531/0208* (2013.01); *B01J 2531/824* (2013.01); *B01J 2531/842* (2013.01)

(58) Field of Classification Search
IPC .................. C07C 67/38; C07F 9/587,9/5726
See application file for complete search history.

(56) References Cited

U.S. PATENT DOCUMENTS

| | | | | |
|---|---|---|---|---|
| 7,435,840 | B2* | 10/2008 | Pfaltz | C07F 9/65848 502/102 |
| 7,994,355 | B2* | 8/2011 | Chen | B01J 31/1845 502/152 |
| 2012/0178963 | A1 | 7/2012 | Clarke et al. | |
| 2013/0331576 | A1 | 12/2013 | Korenaga et al. | |
| 2014/0309435 | A1 | 10/2014 | Franke et al. | |
| 2017/0022137 | A1 | 1/2017 | Dong et al. | |
| 2017/0022138 | A1 | 1/2017 | Dong et al. | |
| 2017/0022139 | A1 | 1/2017 | Dong et al. | |
| 2017/0022234 | A1 | 1/2017 | Jennerjahn et al. | |
| 2017/0022235 | A1 | 1/2017 | Dong et al. | |

FOREIGN PATENT DOCUMENTS

| | | |
|---|---|---|
| EP | 0 662 467 A1 | 7/1995 |
| EP | 1 029 839 A1 | 8/2000 |
| KR | 20120127435 A | 11/2012 |
| WO | 2011/083305 A1 | 7/2011 |

OTHER PUBLICATIONS

Databases Registry, Chemical Abstract Services, STN Accession No. 123133-51-7, Oct. 13, 1984, (1 page).
Databases Registry, Chemical Abstract Services, STN Accession No. 69389-34-0, Nov. 16, 1984, (1 page).
Databases Registry, Chemical Abstract Services, STN Accession No. 69389-35-1, Nov. 16, 1984, (1 page).
European Search Report dated Jan. 2, 2017 for EP 16180047 (1 page).
Buhling, Armin et. al. Novel Amphiphilic Diphosphines: Synthesis, X-ray Structure, Rhodium Complexes, Use in Hydroformylation, and Rhodium Recycling. Organometallics 1997, 16, 3027-3037.
Doherty, Simon et al. The first insoluble polymer-bound palladium complexes of 2-pyridyldiphenylphosphine: highly efficient catalysts for the alkoxycarbonylation of terminal alkynes. Chemical Communications 2006. 88-90.
Bianchini, Claudio et al. Methoxycarbonylation 1-15 of Ethene by Palladium(II) Complexes With 1,1'-Bis(diphenylphosphino) Ferrocene (dppf) and 1,1'-Bis(diphenylphosphino) Octamethylferrocene (dppomf). Organometallics, American Chemical Society, 2003, 2409-2421.
U.S. Appl. No. 15/213,435, Jennerjahn, et al., filed Jul. 19, 2016.
U.S. Appl. No. 15/213,441, Dong, et al., filed Jul. 19, 2016.
U.S. Appl. No. 15/213,444, Dong, et al., filed Jul. 19, 2016.
U.S. Appl. No. 15/213,449, Dong, et al., filed Jul. 19, 2016.
U.S. Appl. No. 15/213,453, Dong, et al., filed Jul. 19, 2016.
Khokarale, S. G. et al. Zwitterion enhanced performance in palladium-phosphine catalyzed ethylene methoxycarbonylation. Catalysis Communications 44, 2014, pp. 73-75.
Clegg, William, et al. Highly active and selective catalysts for the production of methyl propanoate via the methoxycarbonylation of ethane. Chem. Commun. 1999, pp. 1877-1878.
Armarego, Wilfred L.F., et al. Purification of Laboratory Chemicals, Butterworth Heinemann (Elsevier), 6th edition, Oxford 2009. (index provided).
Harris, Robin K. et al. NMR Nomenclature, Nuclear Spin Properties and Conventions for Chemical Shifts. Pure Appl. Chem., 2001, 73, pages 1795-1818.
Harris, Robin K. et al. Further Conventions for NMR Shielding and Chemical Shifts. Pure Appl. Chem., 2008, 80, pages 59-84.
Köppe, Ralf, et al. Quntenchemische and Experimentelle Untersuchungen zur Stabilität and Struktur von $GaAs_5$ und $InAs_5$. Angew. Chem. 2004, 43, 2222-2226.
Allouch, Fatima, et. al. Ferrocenyl (P,N)-diphosphines incorporating pyrrolyl, imidazolyl or benzazaphospholyl moieties: Synthesis, coordination to group 10 metals and performances in palladium-catalyzed arylation reactions. Journal of Organometallic Chemistry No. 735, 2013. pp. 38-46.
Budzelaar, Peter H.M. et al. Synthesis and Coordination Chemistry of a New Class of Binucleating Ligands: Pyridyl-Substituted Diphosphines. Organometallics 1990, 9, 1222-1227.
I.E. Nifantev, et al., Metallocenephosphoramides, 2. * Amides of Ferrocenephosphonous and Ferrocenediphosphonous Acids. Phosphorus, Sulfur, and Silicon. 1992, vol. 68, pp. 99-106.
Written Opinion of the Intellectual Property Office of Singapore for Application No. SG 10201605921S dated Nov. 16, 2017 (5 pages).
Marchenko et al. Stable N-Heterocyclic Carbenes: N-Alkyl-N' phosphanylbenzimidazol-2-ylidenes. European Journal of Organic Chemistry, 2012, pp. 4018-4033.
Office Action dated Nov. 8, 2017 for Canadian Patent Application No. 2,936,323 (4 pages).
Written Opinion of the Intellectual Property Office of Singapore dated May 22, 2017 for Singapore Patent Application No. 10201605921S.
Taiwan Office Action dated Mar. 12, 2018 for TW Patent Application No. 105122755 (2 pages).
Štěpnička, P. et al. Synthesis, Structural Characterization, and Catalytic Evaluation of Palladium Complexes with Homologous Ferrocene-Based Pyridylphosphine Ligands. Organometallics, 29, 2010, pp. 3187-3200.

* cited by examiner

FERROCENE-BASED COMPOUNDS AND PALLADIUM CATALYSTS BASED THEREON FOR THE ALKOXYCARBONYLATION OF ETHYLENICALLY UNSATURATED COMPOUNDS

The present invention relates to novel ferrocene-based compounds and to the use thereof in alkoxycarbonylation.

The alkoxycarbonylation of ethylenically unsaturated compounds is a process of increasing significance. An alkoxycarbonylation is understood to mean the reaction of ethylenically unsaturated compounds such as olefins with carbon monoxide and alcohols in the presence of a metal or metal complex and a ligand to give the corresponding esters:

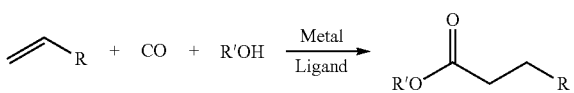

Scheme 1: General Reaction Equation of the Alkoxycarbonylation of an Ethylenically Unsaturated Compound Among the alkoxycarbonylation reactions, ethene methoxycarbonylation to give 3-methylpropionate is of significance as an intermediate stage for the preparation of methyl methacrylate (S. G. Khokarale, E. J. García-Suárez, J. Xiong, U. V. Mentzel, R. Fehrmann, A. Riisager, Catalysis Communications 2014, 44, 73-75). Ethene methoxycarbonylation is conducted in methanol as solvent under mild conditions with a palladium catalyst modified by phosphine ligands.

A very good catalytic system was developed by Lucite—now Mitsubishi Rayon—and uses a ligand based on 1,2-bis(di-tert-butylphosphinomethyl)benzene (DTBPMB) (W. Clegg, G. R. Eastham, M. R. J. Elsegood, R. P. Tooze, X. L. Wang, K. Whiston, Chem. Commun. 1999, 1877-1878).

Applications of methoxycarbonylation to longer-chain substrates are described, for example, in EP 0 662 467. The patent specification describes a process for preparing dimethyl adipate from methyl 3-pentanoate. The Pd source used is Pd(II) acetate. Examples of suitable bidentate phosphine ligands that are cited include 1,1'-bis(diphenylphosphino)ferrocene, 1-(diphenylphosphino)-1'-(diisopropylphosphino)ferrocene and 1,1'-bis(isopropylphenylphosphino)ferrocene. However, the ligands achieve only unsatisfactory yields in the methoxycarbonylation of olefins, especially of long-chain olefins such as 2-octene and di-n-butene.

The technical problem on which the present invention was based is that of providing novel ferrocene-based compounds as ligands for alkoxycarbonylation reactions. These compounds are to achieve improved yields especially in the conversion of long-chain olefins such as 2-octene or di-n-butene. More particularly, the space-time yield is to be increased in the alkoxycarbonylation reaction.

This problem is solved by diphosphine compounds of formula (I)

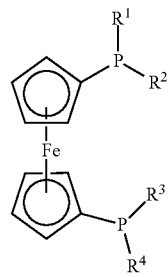

where
$R^1$, $R^2$, $R^3$, $R^4$ are each independently selected from —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl;

at least one of the $R^1$, $R^2$, $R^3$, $R^4$ radicals is a —$(C_6-C_{20})$-heteroaryl radical having at least six ring atoms;
and $R^1$, $R^2$, $R^3$, $R^4$, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_{12})$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})$-alkyl$]_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen.

The compounds according to the invention are suitable as bidentate phosphine ligands for Pd complexes with which high yields can be achieved in the alkoxycarbonylation of a multitude of ethylenically unsaturated compounds. More particularly, the compounds according to the invention are suitable for alkoxycarbonylation of long-chain olefins such as 1-octene or di-n-butene.

The expression $(C_1-C_{12})$-alkyl encompasses straight-chain or branched alkyl groups having 1 to 12 carbon atoms. These are preferably $(C_1-C_8)$-alkyl groups, more preferably $(C_1-C_6)$-alkyl, most preferably $(C_1-C_4)$-alkyl.

Suitable $(C_1-C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1-C_{12})$-alkyl also apply correspondingly to the alkyl groups in —O—$(C_1-C_{12})$-alkyl, —S—$(C_1-C_{12})$-alkyl, —COO—$(C_1-C_{12})$-alkyl, —CONH—$(C_1-C_{12})$-alkyl, —CO—$(C_1-C_{12})$-alkyl and —N—$[(C_1-C_{12})$-alkyl$]_2$.

The expression $(C_3-C_{12})$-cycloalkyl encompasses mono-, bi- or tricyclic hydrocarbyl groups having 3 to 12 carbon atoms. Preferably, these groups are $(C_5-C_{12})$-cycloalkyl.

The $(C_3-C_{12})$-cycloalkyl groups have preferably 3 to 8, more preferably 5 or 6, ring atoms.

Suitable $(C_3-C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3-C_{12})$-cycloalkyl also apply correspondingly to the cycloalkyl groups in —O—$(C_3-C_{12})$-cycloalkyl, —S—$(C_3-C_{12})$-cycloalkyl, —COO—$(C_3-C_{12})$-cycloalkyl, —CONH—$(C_3-C_{12})$-cycloalkyl, —CO—$(C_3-C_{12})$-cycloalkyl.

The expression $(C_3-C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3-C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_6-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression $(C_3-C_{20})$-heteroaryl also encompasses $(C_6-C_{20})$-heteroaryl radicals having at least six ring atoms.

The expression $(C_6-C_{20})$-heteroaryl having at least six ring atoms encompasses mono- or polycyclic aromatic hydrocarbyl radicals having 6 to 20 carbon atoms, where one or more of the carbon atoms are replaced by heteroatoms. Preferred heteroatoms are N, O and S. The $(C_6-C_{20})$-heteroaryl groups have 6 to 14 and more preferably 6 to 10 ring atoms.

Suitable $(C_6-C_{20})$-heteroaryl groups having at least six ring atoms are especially pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, are each independently substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, are each independently substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, are each independently substituted by one or more substituents selected from —$(C_1-C_{12})$-alkyl, —O—$(C_1-C_{12})$-alkyl-$(C_6-C_{20})$-aryl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, are each independently substituted by one or more substituents selected from —$(C_1-C_{12})$-alkyl and —$(C_3-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, or —$(C_3-C_{12})$-heterocycloalkyl, and may be substituted as described if they are —$(C_6-C_{20})$-aryl, —$(C_3-C_{20})$-heteroaryl or —$(C_6-C_{20})$-heteroaryl.

In one embodiment, the $R^1$, $R^2$, $R^3$, $R^4$ radicals are unsubstituted if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl.

In one embodiment, $R^1$, $R^2$, $R^3$, $R^4$ are each independently selected from —$(C_1-C_{12})$-alkyl, —$(C_6-C_{20})$-aryl, —$(C_3-C_{20})$-heteroaryl;

where at least one of the $R^1$, $R^2$, $R^3$, $R^4$ radicals is a —$(C_6-C_{20})$-heteroaryl radical having at least six ring atoms;

and $R^1$, $R^2$, $R^3$, $R^4$, if they are —$(C_1-C_{12})$-alkyl, —$(C_6-C_{20})$-aryl, —$(C_3-C_{20})$-heteroaryl or —$(C_6-C_{20})$-heteroaryl, may independently be substituted by one or more of the above-described substituents.

In one embodiment, at least two of the $R^1$, $R^2$, $R^3$, $R^4$ radicals are a —$(C_6-C_{20})$-heteroaryl radical having at least six ring atoms.

In one embodiment, the $R^1$ and $R^3$ radicals are each a —$(C_6-C_{20})$-heteroaryl radical having at least six ring atoms and may each independently be substituted by one or more of the substituents described. Preferably, $R^2$ here is a —($C_6$-$C_{20}$)-heteroaryl radical having at least six ring atoms or is selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, most preferably from —($C_1$-$C_{12}$)-alkyl, —($C_3$-$C_{12}$)-cycloalkyl, —($C_6$-$C_{20}$)-aryl. $R^4$ here is preferably selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, most preferably from —($C_1$-$C_{12}$)-alkyl, —($C_3$-$C_{12}$)-cycloalkyl, —($C_6$-$C_{20}$)-aryl.

In one embodiment, the $R^1$ and $R^3$ radicals are each a —($C_6$-$C_{20}$)-heteroaryl radical having at least six ring atoms and $R^2$ and $R^4$ are selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl. $R^1$, $R^2$, $R^3$, $R^4$ here may each independently be substituted by one or more of the above-described substituents.

More preferably, the $R^1$ and $R^3$ radicals are each a —($C_6$-$C_{20}$)-heteroaryl radical having at least six ring atoms and $R^2$ and $R^4$ are —($C_1$-$C_{12}$)-alkyl. $R^1$, $R^2$, $R^3$, $R^4$ here may each independently be substituted by one or more of the above-described substituents.

In one embodiment, the $R^1$, $R^2$, $R^3$ radicals are each a —($C_6$-$C_{20}$)-heteroaryl radical having at least six ring atoms and may each independently be substituted by one or more of the substituents described above. Preferably, $R^4$ here is not a —($C_3$-$C_{20}$)-heteroaryl radical. More preferably, $R^4$ here is selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, most preferably from —($C_1$-$C_{12}$)-alkyl, —($C_3$-$C_{12}$)-cycloalkyl, —($C_6$-$C_{20}$)-aryl.

In one embodiment, the $R^1$, $R^2$, $R^3$ and $R^4$ radicals are each a —($C_6$-$C_{20}$)-heteroaryl radical having at least six ring atoms and may each independently be substituted by one or more of the substituents described above.

In one embodiment, the $R^1$, $R^2$, $R^3$ and $R^4$ radicals, if they are a heteroaryl radical, are each independently selected from heteroaryl radicals having six to ten ring atoms.

In one embodiment, the $R^1$, $R^2$, $R^3$ and $R^4$ radicals, if they are a heteroaryl radical, are a heteroaryl radical having six ring atoms.

Preferably, the $R^1$, $R^2$, $R^3$ and $R^4$ radicals, if they are a heteroaryl radical, are each independently selected from pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, the $R^1$, $R^2$, $R^3$ and $R^4$ radicals, if they are a heteroaryl radical, are each independently selected from pyridyl, pyrimidyl, indolyl, where the heteroaryl radicals mentioned may be substituted as described above.

Preferably, the $R^1$, $R^2$, $R^3$ and $R^4$ radicals, if they are a heteroaryl radical, are each independently selected from 2-pyridyl, 2-pyrimidyl, 2-indolyl, where the heteroaryl radicals mentioned may be substituted as described above.

Preferably, the $R^1$, $R^2$, $R^3$ and $R^4$ radicals, if they are a heteroaryl radical, are each independently selected from 2-pyridyl, 2-pyrimidyl, N-phenyl-2-indolyl, 2-indolyl, where the heteroaryl radicals mentioned have no further substitution.

In one embodiment, the $R^1$ and $R^3$ radicals are each a heteroaryl radical selected from pyridyl and pyrimidyl, especially 2-pyridyl and 2-pyrimidyl.

where the $R^2$ and $R^4$ radicals are each independently selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl;

and $R^1$ and $R^3$, and $R^2$ and $R^4$, if they are —($C_1$-$C_{12}$)-alkyl, —($C_3$-$C_{12}$)-cycloalkyl, —($C_3$-$C_{12}$)-heterocycloalkyl or —($C_6$-$C_{20}$)-aryl, may each independently be substituted by one or more of the above-described substituents.

In one embodiment, the $R^1$ and $R^3$ radicals are each a heteroaryl radical having six ring atoms, and the $R^2$ and $R^4$ radicals are each —($C_1$-$C_{12}$)-alkyl;

where $R^1$, $R^3$ may each independently be substituted by one or more of the above-described substituents.

In one embodiment, the compound has a structure of one of the formulae (8), (14) and (15):

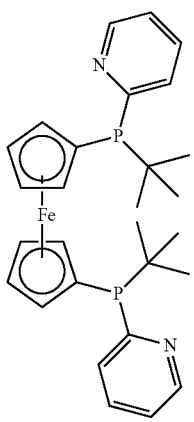

(8)

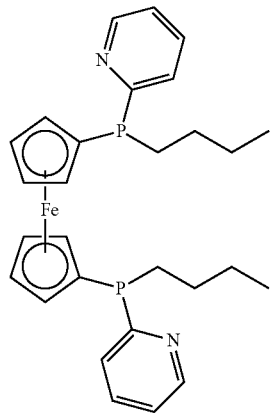

(14)

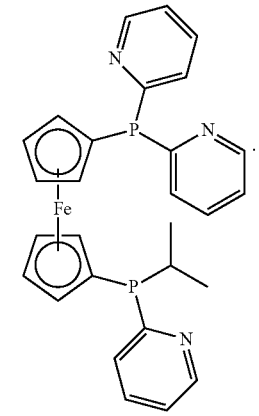

(15)

The diphosphine compounds according to the invention can be obtained, for example, by reaction of ferrocene with butyllithium and a chlorophosphine compound.

The invention thus likewise relates to novel chlorophosphine compounds which can be used as a precursor for synthesis of the diphosphine compounds according to the invention. The chlorophosphine compounds according to the invention have the formula (II)

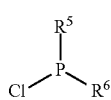

(II)

where $R^5$ is a —$(C_6$-$C_{20})$-heteroaryl radical having at least six ring atoms;

$R^6$ is selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl;

and $R^5$ and $R^6$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl or —$(C_6$-$C_{20})$-heteroaryl radical, may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —SO$_3$H, —NH$_2$, halogen.

In one embodiment, the $R^5$ and $R^6$ radicals, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl or —$(C_6$-$C_{20})$-heteroaryl, may each be independently substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —SO$_3$H, —NH$_2$, halogen.

In one embodiment, the $R^5$ and $R^6$ radicals, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl or —$(C_6$-$C_{20})$-heteroaryl, may each be independently substituted by one or more substituents selected from —$(C_1$-$C_{12})$-alkyl, —$(C_3$-$C_{12})$-cycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl.

In one embodiment, the $R^5$ and $R^6$ radicals, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl or —$(C_6$-$C_{20})$-heteroaryl, may each independently be substituted by one or more substituents selected from —$(C_1$-$C_{12})$-alkyl and —$(C_3$-$C_{20})$-heteroaryl.

In one embodiment, $R^6$ is unsubstituted if it is —$(C_1$-$C_{12})$-alkyl, —$(C_3$-$C_{12})$-cycloalkyl, or —$(C_3$-$C_{12})$-heterocycloalkyl, and may be substituted as described if $R^6$ is —$(C_6$-$C_{20})$-aryl, —$(C_3$-$C_{20})$-heteroaryl or —$(C_6$-$C_{20})$-heteroaryl.

In one embodiment, the $R^5$ and $R^6$ radicals are unsubstituted.

In one embodiment, $R^6$ is selected from —$(C_1$-$C_{12})$-alkyl, —$(C_6$-$C_{20})$-aryl, —$(C_3$-$C_{20})$-heteroaryl. More preferably, $R^6$ is selected from —$(C_1$-$C_{12})$-alkyl, where $R^6$ may be substituted as described above.

In one embodiment, $R^5$ is a heteroaryl radical having six to ten ring atoms. Preferably, $R^5$ is a heteroaryl radical having six ring atoms.

In one embodiment, $R^5$ is selected from pyridyl, pyridazinyl, pyrimidyl, pyrazinyl, benzofuranyl, indolyl, isoindolyl, benzimidazolyl, quinolyl, isoquinolyl, where the heteroaryl radicals mentioned may also be substituted as described above. Preferably, $R^5$ is selected from 2-pyridyl, 2-pyrimidyl, 2-indolyl, where the heteroaryl radicals mentioned may also be substituted as described above. More preferably, $R^5$ is selected from 2-pyridyl, 2-pyrimidyl, N-phenyl-2-indolyl, 2-indolyl, where the heteroaryl radicals mentioned have no further substitution. Most preferably, $R^5$ is selected from pyridyl and pyrimidyl, especially 2-pyridyl and 2-pyrimidyl.

In one embodiment, the chlorophosphine compound is chloro-2-pyridyl-tert-butylphosphine.

The invention further relates to complexes comprising Pd and a diphosphine compound according to the invention. In these complexes, the diphosphine compound according to the invention serves as a bidentate ligand for the metal atom. The complexes serve, for example, as catalysts for alkoxycarbonylation. With the complexes according to the invention, it is possible to achieve high yields in the alkoxycarbonylation of a multitude of different ethylenically unsaturated compounds.

The complexes according to the invention may also comprise further ligands which coordinate to the metal atom. These are, for example, ethylenically unsaturated compounds or anions. Suitable additional ligands are, for example, styrene, acetate anions, maleimides (e.g. N-methylmaleimide), 1,4-naphthoquinone, trifluoroacetate anions or chloride anions.

The invention further relates to the use of a diphosphine compound according to the invention for catalysis of an alkoxycarbonylation reaction. The compound according to the invention can especially be used as a metal complex according to the invention.

The invention also relates to a process comprising the process steps of:
a) initially charging an ethylenically unsaturated compound;
b) adding a diphosphine compound according to the invention and a compound comprising Pd, or adding a complex according to the invention comprising Pd and a diphosphine compound according to the invention;

c) adding an alcohol;
d) feeding in CO;
e) heating the reaction mixture, with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

In one embodiment, the ethylenically unsaturated compound comprises 4 to 30 carbon atoms, preferably 6 to 22 carbon atoms, more preferably 8 to 12 carbon atoms, most preferably 8 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

In a particularly preferred embodiment, the ethylenically unsaturated compound is an unfunctionalized alkene having at least one double bond and 2 to 30 carbon atoms, preferably 6 to 22 carbon atoms, further preferably 8 to 12 carbon atoms, and most preferably 8 carbon atoms.

Suitable ethylenically unsaturated compounds are, for example:
ethene;
propene;
C4 olefins such as 1-butene, cis-2-butene, trans-2-butene, mixture of cis- and trans-2-butene, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins;
triisobutene, tri-n-butene;
terpenes such as limonene, geraniol, farnesol, pinene, myrcene, carvone, 3-carene; polyunsaturated compounds having 18 carbon atoms, such as linoleic acid or linolenic acid;
esters of unsaturated carboxylic acids, such as vinyl esters of acetic or propionic acid, alkyl esters of unsaturated carboxylic acids, methyl or ethyl esters of acrylic acid and methacrylic acid, oleic esters, methyl or ethyl oleate, esters of linoleic or linolenic acid;
vinyl compounds such as vinyl acetate, vinylcyclohexene, styrene, alpha-methylstyrene, 2-isopropenylnaphthalene;
2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butene, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which have to be removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex according to the invention. The Pd complex may either be added in process step b) as a preformed complex comprising Pd and the phosphine ligands according to the invention or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In the case of the complex which is added right at the start as well, it is also possible to add further ligand, such that the unbound ligand is present in the reaction mixture.

In one variant, the compound comprising Pd is selected from palladium dichloride ($PdCl_2$), palladium(II) acetylacetonate [$Pd(acac)_2$], palladium(II) acetate [$Pd(OAc)_2$], dichloro(1,5-cyclooctadiene)palladium(II) [$Pd(cod)_2Cl_2$], bis(dibenzylideneacetone)palladium [$Pd(dba)_2$], bis(acetonitrile)dichloropalladium(II) [$Pd(CH_3CN)_2Cl_2$], palladium(cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one embodiment, the alcohol is an alkanol having one or more hydroxyl groups and 1 to carbon atoms, preferably 1 to 22 carbon atoms, more preferably 1 to 12 carbon atoms, most preferably 1 to 6 carbon atoms.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, triols, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred variant of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C., in order to convert the ethylenically unsaturated compound to an ester.

The molar ratio of the ethylenically unsaturated compound initially charged in step a) to the alcohol added in step c) is preferably between 1:1 and 1:20, more preferably 1:2 and 1:10, more preferably 1:3 and 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the diphosphine compound according to the invention to Pd is preferably between 0.1:1 and 400:1, preferably between 0.5:1 and 400:1, more preferably between 1:1 and 100:1, most preferably between 2:1 and 50:1.

Preferably, the process is conducted with addition of an acid. In one variant, the process therefore additionally comprises step c'): adding an acid to the reaction mixture. This may preferably be a Brønsted or Lewis acid.

Suitable Brønsted acids preferably have a $pK_a \leq 5$, preferably an acid strength of $pK_a \leq 3$. The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

Preferably, the acid is not a carboxylic acid.

Suitable Brønsted acids are, for example, perchloric acid, sulphuric acid, phosphoric acid, methylphosphonic acid and sulphonic acids. Preferably, the acid is sulphuric acid or a sulphonic acid. Suitable sulphonic acids are, for example, methanesulphonic acid, trifluoromethanesulphonic acid, tert-butanesulphonic acid, p-toluenesulphonic acid (PTSA), 2-hydroxypropane-2-sulphonic acid, 2,4,6-trimethylbenzenesulphonic acid and dodecylsulphonic acid. Particularly preferred acids are sulphuric acid, methanesulphonic acid, trifluoromethanesulphonic acid and p-toluenesulphonic acid.

A Lewis acid used may, for example, be aluminium triflate.

In one embodiment, the amount of acid added in step c') is 0.3 to 40 mol %, preferably 0.4 to 15 mol %, more preferably 0.5 to 5 mol %, most preferably 0.6 to 3 mol %, based on the molar amount of the ethylenically unsaturated compound used in step a).

EXAMPLES

Figure 1:
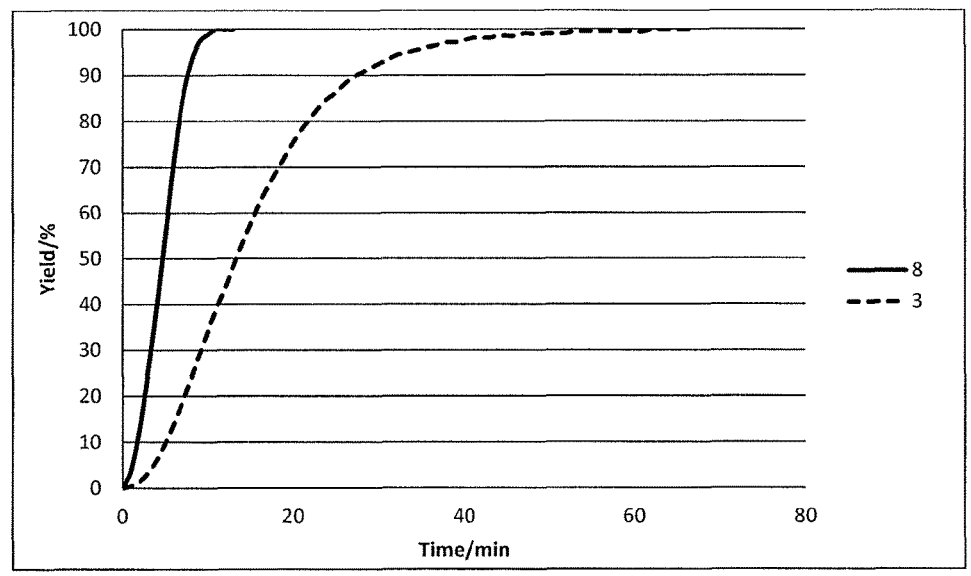
FIG. 1 methoxycarbonylation of ethene with 3 and 8 at 80° C. and 40 bar CO

The invention is described in detail hereinafter by working examples.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (δ) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.

Preparation of Precursor E

Preparation of chloro-2-pyridyl-tert-butylphosphine

The Grignard for the synthesis of chloro-2-pyridyl-t-butylphosphine is prepared by the "Knochel method" with isopropylmagnesium chloride (Angew. Chem. 2004, 43, 2222-2226). The workup is effected according to the method of Budzelaar (Organometallics 1990, 9, 1222-1227).

Scheme 2: Synthesis of precursor E

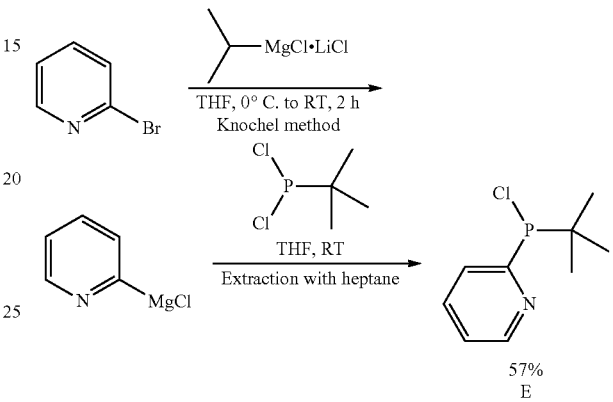

8.07 ml of a 1.3 M isopropylmagnesium chloride solution (Knochel's reagent) are introduced under argon into a 50 ml round-bottom flask with magnetic stirrer and septum, and cooled to −15° C. Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which have been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1$H NMR (300 MHz, $C_6D_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu)

$^{13}$C NMR (75 MHz, $C_6D_6$): δ 162.9, 162.6, 148.8, 135.5, 125.8, 125.7, 122.8, 35.3, 34.8, 25.9 and 25.8.

$^{31}$P NMR (121 MHz, $C_6D_6$) δ 97.9.

MS (EI) m:z (relative intensity) 201 (M$^+$, 2), 147(32), 145 (100), 109 (17), 78 (8), 57.1 (17).

Preparation of Compound 8

Preparation of 1,1'-bis(tert-butyl-2-pyridylphosphino)ferrocene

Scheme 3: Synthesis of compound 8

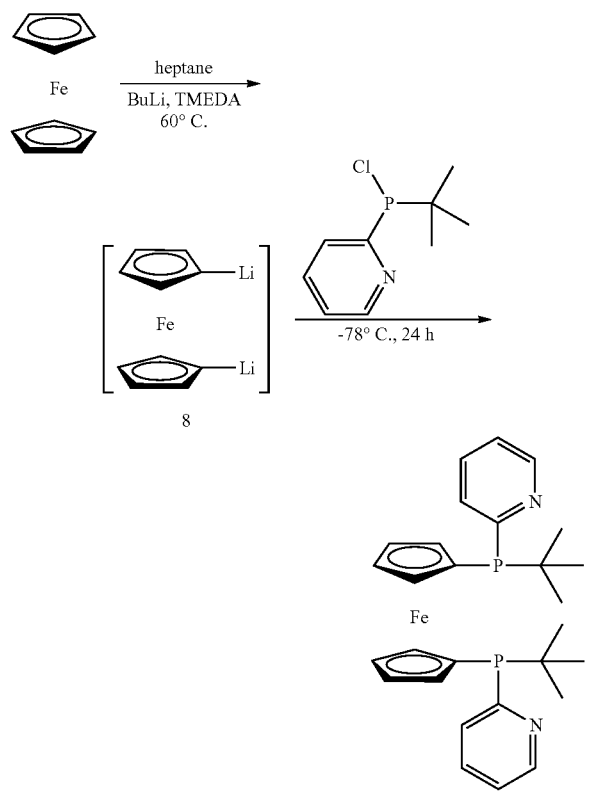

Variant A:

474.4 mg (2.55 mmol) of sublimed ferrocene are weighed into a 50 ml round-bottom flask with magnetic stirrer and septum, and the flask was purged. After addition of 15 ml of heptane, the ferrocene has dissolved completely. Then 841 µl of tetramethylethylenediamine (1.1 eq, 5.61 mmol) are added all at once and 2.04 ml of BuLi (2.5 M in hexane, 2.0 eq, 5.1 mmol) are added dropwise. After 2-3 hours, an orange solid precipitates out. The mixture is left to stir overnight, the heptane solution is decanted and the orange solid is washed twice with heptane. Then another 10 ml of heptane are added and the suspension is cooled to −70° C. 1.08 g (2.1 eq, 5.36 mmol) of chloro-2-pyridyl-tert-butylphosphine are dissolved in 7 ml of heptane. The solution is cloudy and has to be filtered through Celite. A little insoluble white solid has formed. This solution is added dropwise to the dilithioferrocene solution. While being warmed up to room temperature, the colour of the orange suspension lightens. To complete the reaction, the reaction solution is heated under reflux for about 1 hour. A clear orange solution and white precipitate have formed.

7 ml of argon-saturated water are added to the suspension. The white precipitate dissolves. After the aqueous phase has been removed, the operation is repeated twice. This makes the heptane phase cloudy. On completion of removal of the organic phase under high vacuum, what remains is an orange oily residue. This is taken up in 10 ml of ether and dried over $Na_2SO_4$. (Crude yield 913 mg.) At −28° C., there is no formation of either a precipitate or crystals overnight. Nor does a mixture of diethyl ether and heptane lead to crystallization at −28° C. A $^{31}$P NMR of the solution again shows the product peak, now at 7.39 ppm, and a signal at 40.4 ppm. The product can be purified by column chromatography. The ether solution is applied to a short column which is eluted with diethyl ether under argon. The orange product front runs off right at the front and can be collected easily. After the ether has been removed, 241 mg (16%) of an orange viscous oil are obtained in about 95% purity.

Variant B:

Batch size: 650.17 mg (3.495 mol) of ferrocene (sublimed), 2.8 ml (2 eq, 6.99 mmol) of 2.5 M BuLi (n-butyllithium), 1.1 ml (2.1 eq, 7.3 mmol) of tetramethylethylenediamine and 1.48 g (2.1 eq, 7.34 mmol) of chloro-2-pyridyl-tert-butylphosphine.

The dilithium salt of ferrocene is again prepared in 15 ml of heptane. The chloro-2-pyridyl-tert-butylphosphine is dissolved in 10 ml of THF rather than heptane, because the chlorophosphine dissolves better in THF. The workup was likewise optimized: after boiling under reflux, the reaction mixture is quenched with only 1 ml of $H_2O$ and the solvent (heptane and THF) is removed completely under high vacuum. The dark yellow/orange stringy solid is taken up in 8 ml of $H_2O$ and 15 ml of dimethyl ether and stirred for 1 minute. After phase separation, the aqueous phase is removed via a syringe and the organic phase is washed three times with $H_2O$. The organic phase is dried over $Na_2SO_4$ and filtered. The product is washed out of the $Na_2SO_4$ 3 times with 10 ml each time of diethyl ether until the solution is almost colourless. The dark orange solution is concentrated to a volume of 10 ml and sent through a column comprising silica gel 60 under argon. The eluent used is diethyl ether again. The filtrate is much brighter and more orange. After removing the solid, 1.16 g of a stringy orange solid are obtained. (64%)

Preparation of Compound 10

Comparative Compound

Proceeding from 1,1'-(ferrocenediyl)phenylphosphine, the strained phosphine ring is opened with PhLi and the resulting intermediate is quenched with a chlorophosphine.

Scheme 4: Synthesis of a ferrocenyl ligand

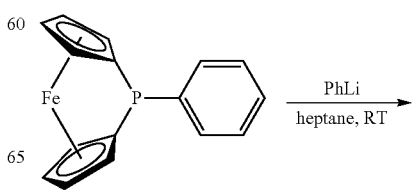

-continued

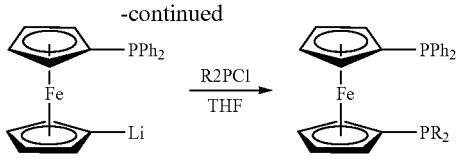

Scheme 5: Synthesis of compound 10

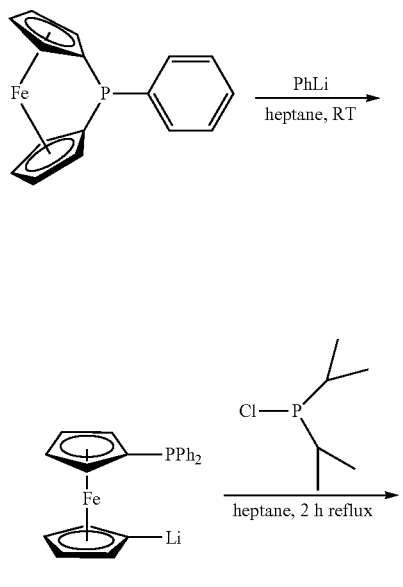

A 50 ml round-bottom flask with magnetic stirrer bar and nitrogen connection is initially charged with 1.13 mmol (565 µl) of phenyllithium (PhLi), and a solution of 1.03 mmol (300 mg) of cyclic phosphine in 20 ml of heptane is slowly added dropwise via a syringe pump. The Li salt is washed twice with heptane and admixed with 6 ml of heptane. A heptane solution of 0.8 eq (0.824 mmol, 131 µl) of ClPiPr$_2$ in 7 ml of heptane is added dropwise to the suspension at room temperature. The red-brown suspension barely changes colour. After stirring for 20 min, the suspension is heated under reflux for 1.5 hours. The solid turns a somewhat lighter colour. Solvent is removed completely and the brown-red residue is taken up in H$_2$O and ether. The organic phase is washed twice with H$_2$O and dried over Na$_2$SO$_4$. A $^{31}$P spectrum of the ether phase is recorded. The spectrum shows 2 singlets. The chlorophosphine has been fully consumed. The ether phase is dried and 300 mg (yield: 61%) of a brown-yellow oil are obtained, which dissolves in MeOH on a water bath at 65° C. The solution is put in the freezer (−78° C.) overnight. 76 mg of a brown-yellow oil precipitate out, which is analysed by NMR spectroscopy.

$^1$H NMR (300 MHz, CDCl$_3$) δ 7.46-7.23 (m, 10H, Ph), 4.36 (m, 2H, Cp), 4.21 (m, 2H, Cp), 34.24 (m, 4H, Cp), 1.88 (m, 2H, iPr), 1.15-0.96 (m, 12H, iPr).

$^{13}$C NMR (75 MHz, CDCl$_3$) δ 139.9 (J=9.8 Hz, Ph), 133.4 (J=19.2 Hz, Ph), 128.4, 128.1, 128.0 (Ph), 77.1, 76.8, 76.2, 76.1 (Cp), 73.5 (J=14.5 Hz, Cp), 72.8 (J=2.9 Hz, Cp), 71.9 (J=10.5 Hz, Cp), 72.1 (Cp), 23.3 (J=11.0 Hz, iPr), 20.1, 20.0, 19.9, 19.8 (iPr).

$^{31}$P NMR (121 MHz, C$_6$D$_6$) δ=0.88 and −16.62

Preparation of Compound 14

Preparation of bis(2-pyridyl-n-butylphosphino)ferrocene

Scheme 6: Synthesis of compound 14

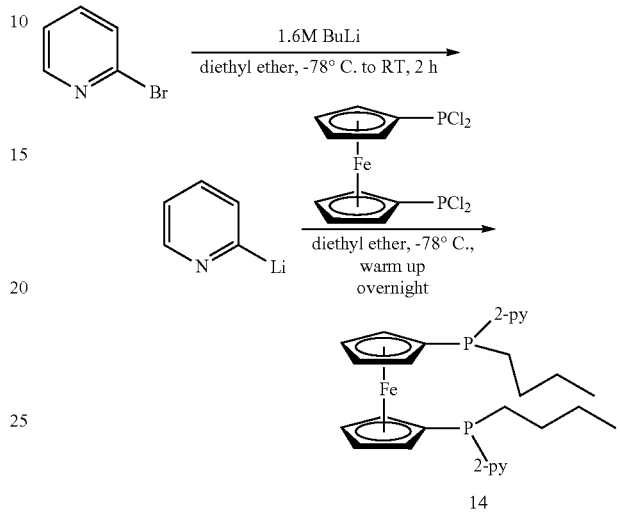

In a 25 ml round-bottom flask with magnetic stirrer bar and tap, 1.45 ml (2.33 mmol) of 1.6 M BuLi are cooled to −78° C. (dry ice/EtOH). To this are added dropwise 208 µl (2.18 mmol) of 2-bromopyridine dissolved in 2 ml of ether. The reaction solution turns yellow at first, then changes colour to orange, but remains clear. After stirring for 15 minutes, a sample (100 µl) is taken and quenched with NH$_4$Cl/H$_2$O. According to GC, as well as pyridine, numerous other compounds have also formed. Then, at this temperature, 1,1'-bis(dichlorophosphine)ferrocene dissolved in 2 ml of ether are added dropwise and the reaction mixture is allowed to warm up overnight. A pale orange suspension has formed, which is filtered through a frit (G4). A clear orange ether solution is obtained. After the solvent has been drawn off under reduced pressure, 173 mg of an orange solid are obtained, and this is chromatographed under argon. The mixture is columned first with pure diethyl ether (column parameters: diameter 4 cm, silica gel 60), and 50 mg of a stringy yellow solid are obtained. The solid is columned once again with 2:1 heptane/diethyl ether, and 31 mg of bis(2-pyridyl-n-butylphosphino)ferrocene (18%) are obtained.

$^1$H NMR (300 MHz, C$_6$D$_6$): δ 8.54 (d, J=4.6 Hz, 2H, py), 7.43-7.32 (m, 2H, py), 6.94-6.88 (m, 2H, py), 6.58-6.49 (m, 2H, py), 4.47 (m, 1H, ferrocenyl), 4.37 (m, 1H, ferrocenyl), 4.33 (m, 1H, ferrocenyl), 4.23-4.14 (m, 5H, ferrocenyl), 2.56-2.44 (m, 2H, CH$_2$), 2.23 (m, 2H, CH$_2$), 1.80-1.65 (m, 4H, CH$_2$), 1.57-1.39 (m, 4H, CH$_2$), 0.93-0.85 (m, 6H, CH$_3$).

$^{13}$C NMR (75 MHz, C$_6$D$_6$): δ 166.5, 166.2, 166.1, 150.1, 134.8 and 122.1 (py), 78.7, 78.6, 78.5, 74.9, 74.7, 74.3, 74.1, 72.8, 72.6, 72.1 and 71.7 (ferrocenyl), 29.7, 29.6, 29.5, 29.4, 28.2, 28.1, 27.9, 27.8, 24.8, 24.7, 24.6 and 14.1 (CH$_2$), 14.1 (CH$_3$).

$^{31}$P NMR (121 MHz, C$_6$D$_6$) δ −24.7 and −24.9.

HRMS (ESI) m/z$^+$ calculated for C$_{28}$H$_{34}$FeN$_2$P$_2$(M+H)$^+$ 517.16197. found: 517.16238.

Preparation of Compound 15

Preparation of bis(2-pyridyl-n-butylphosphino)ferrocene

Scheme 7: Synthesis of compound 15

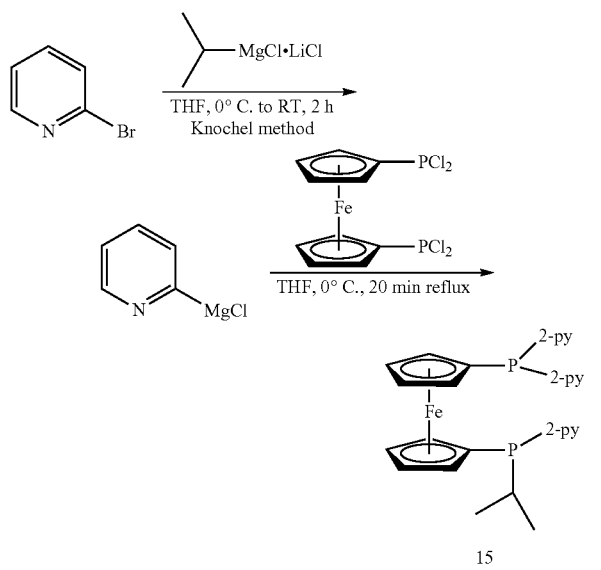

In a 25 ml round-bottom flask with a magnetic stirrer, 5.3 ml (1.1 eq) of a 1.3 M isopropylmagnesium chloride solution (Knochel's reagent) are cooled to −20° C. and added all at once to 603 µl (6.32 mmol) of 2-bromopyridine. The mixture is stirred at −20° C. for one hour and then at room temperature for 2 hours, in order to achieve complete conversion. In a second 50 ml round-bottom flask, 490.7 mg (1.26 mmol) of 1,1'-bis(dichlorophosphino)ferrocene are weighed out in a glovebox and, after removal through the airlock, dissolved in 10 ml of THF. After cooling to −20° C., the previously prepared Grignard compound is added dropwise to the orange-yellow solution by means of a syringe pump. After dropwise addition, the solution has warmed to 00° C. and a brown/black solution has formed. To complete the reaction, the mixture is heated under reflux for another 20 minutes. The next day, 0.5 ml of water is added to the black reaction solution, and the solution lightens in colour to become a dark red/brown suspension. The solvent is drawn off under high vacuum and the residue is taken up in 15 ml of ether and 10 ml of H$_2$O. The suspension is filtered through Celite, and an orange organic phase and a green aqueous phase are obtained. The organic phase is dried over Na$_2$SO$_4$ and, after the ether has been drawn off, 410 mg of a green/black solid are obtained. The dark green, almost black solid is columned in pure diethyl ether. After the ether has been removed, 112 mg of the yellow product 15 are obtained.

$^1$H NMR (300 MHz, C$_6$D$_6$): δ 8.56 (m, 1H, py), 8.48-8.38 (m, 2H, py), 7.58 (m, 1H, py), 7.39-7.27 (m, 2H, py), 7.00-6.84 (m, 3H, py), 6.65-6.56 (m, 1H, py), 6.55-6.44 (m, 2H, py), 4.50-4.39 (m, 3H, ferrocenyl), 4.26-4.18 (m, 2H, ferrocenyl), 4.18-4.12 (m, 1H, ferrocenyl), 4.12-4.04 (m, 2H, ferrocenyl), 2.69 (oct, J=7.0 Hz, 1H ipr), 1.14-0.94 (m, 6H, ipr).

$^{13}$C NMR (75 MHz, C$_6$D$_6$): δ 165.4, 163.7, 150.2, 150.0, 149.9, 134.9, 134.8, 134.7, 131.1, 130.6, 129.1, 128.8, 128.6, 122.7, 122.2, and 122.0 (py), 77.5, 77.3, 76.9, 76.5, 75.4, 75.2, 74.8, 74.6, 74.4, 72.8, 72.7, 72.5, 72.0 and 71.9 (ferrocenyl), 32.2, 28.3, 28.2, 23.0, 20.6, 20.3, 19.7, 19.5 and 14.3 (ipr).

$^{31}$P NMR (121 MHz, C$_6$D$_6$) δ −6.2 and −12.9.

HRMS (ESI) m/z$^+$ calculated for C$_{28}$H$_{27}$FeN$_3$P$_2$(M+H)$^+$ 524.11027. found: 524.11022.

Preparation of Compound 19

Comparative Compound

Scheme 8: Synthesis of compound 19

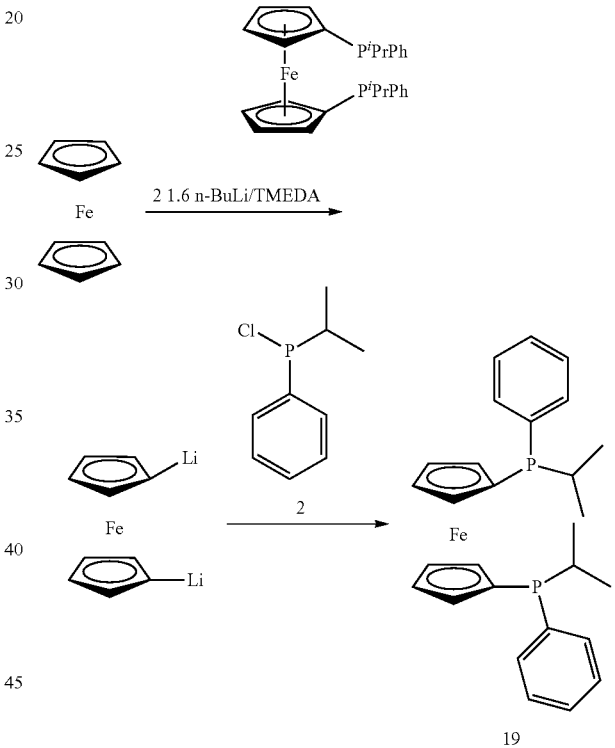

0.93 g of ferrocene is dissolved in 50 ml of absolute heptane in a 100 ml three-neck flask provided with a thermometer, magnetic stirrer and reflux condenser. 1.3 g of TMEDA (1.6 ml) and 7.5 ml of 1.6 M n-BuLi/hexane are added by means of syringes at room temperature. The solution is left to stand for 5 hours. Orange/brown crystals of the dilithiated ferrocene precipitate out. The supernatant solution is removed by means of a syringe. And 20 ml of absolute heptane are added. Subsequently, the chlorophosphine dissolved in 10 ml of heptane is added dropwise. The mixture is heated under reflux for one hour. After cooling, the organic phase is washed three times with 10 ml each time of degassed water. The mixture is concentrated to dryness, and 10 ml of diethyl ether are added. The solution is filtered through 10 cm of silica gel 60 under argon with diethyl ether as solvent, concentrated to dryness and crystallized from a little hot methanol to give the target product in an about 50% non-optimized yield.

Analysis:

$^{31}$P (121 MHz, CDCl$_3$), −7.8 s, −8.15 s, $^{13}$C (75 MHz, CDCl$_3$); 137.77, (d, J=12 Hz), 137.4 (d, J=11.3 Hz), 134.2 (d, J=20.3 Hz), 129.1 s, 128.1 (d, J=7.5 Hz), 77.4 (d, J=11.3 Hz), 75.0 (d, J=26.2 Hz), 74.0 (d, J=22.3 Hz), 72.1 bs, 71.9-71.5 m, 71.1 s, 69.0 s, 27.6 (d, J=10 Hz), 27.55 8d, J=10 Hz), 20.3-19.9 m $^{1}$H (300 MHz, CDCl$_3$): 7.52-7.44 (m, 4H), 7.33-7.23 (m, 6H), 4.23 (sept, J=1.2 Hz, 1H), 4.1-4.0 (m, 4H), 3.93-3.9 (m, 1H), 3.87-3.84 (m, 1H), 3.58-3.54 (m, 1H), 2.1-1.9 (m, 2H), 0.99 (d, J=7 Hz, 3H), 0.94 (d, J=7 Hz, 3H), 0.83-0.7 (m, 6H)

Preparation of Palladium Complexes

Experiment 52: Preparation of Complex K4

Preparation of [Pd(Cp$_2$Fe)1,1'-(P(2-pyridyl)(t-butyl))$_2$]η$^2$-N-methylmaleimide] K4

Scheme 9: Synthesis of complex K4

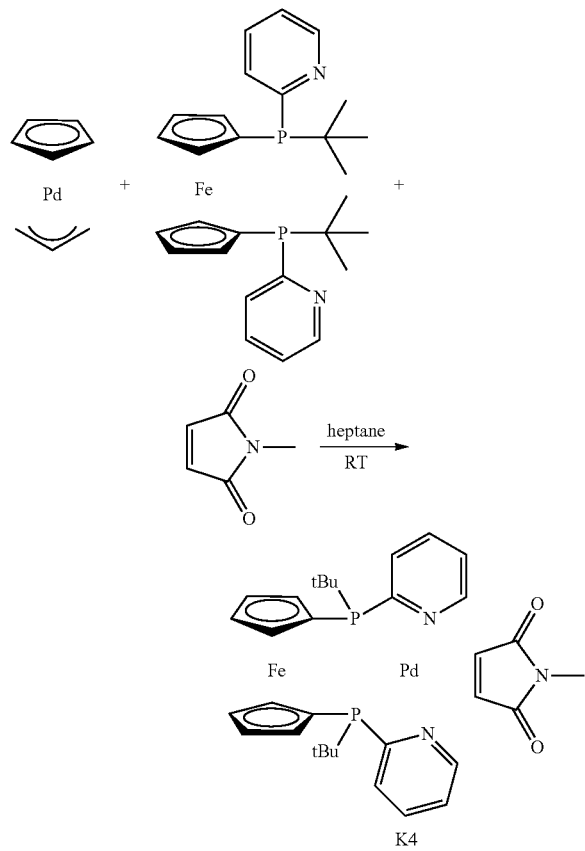

172.9 mg (0.816 mmol) of palladium precursor (see Scheme 9) and 90.64 mg (0.816 mmol) of sublimed N-methylmaleimide (see Experiment 51) are weighed out in each case into a 50 ml Schlenk vessel in a glovebox. 446.6 mg (0.866 mmol) of the viscous orange ferrocene ligand 8 are dissolved in 15 ml of heptane and added to the N-methylmaleimide. The solution is heated to 60° C. on a water bath until everything has dissolved. In order to obtain a clear orange solution, the solution is filtered through Celite. The palladium precursor is likewise dissolved in 10 ml of heptane and filtered through Celite. At room temperature, the clear orange ligand/N-methylmaleimide solution is added dropwise to the deep red palladium precursor. The dark red solution lightens in colour, and a pale yellow solid precipitates out. The mixture is left to stir overnight, and the supernatant solution is decanted after the solids have settled out. After washing with heptane twice, the solid is dried under high vacuum, and 541 mg (86%) of product are obtained.

Elemental analysis calculated for: C$_{33}$H$_{39}$FeN$_3$O$_2$P$_2$Pd: C, 54.01; H, 5.36; N, 5.73; P, 8.44. found: C, 53.44; H, 5.48; N, 5.72; P, 8.48.

High-Pressure Experiments

Feedstocks:

Methanol (MeOH)

Ethene (also referred to as ethylene)

Crack-C4 refers to a by-product stream from what is called the steamcracking process for ethylene production and consists generally to an extent of more than 95% of a mixture of various branched and linear hydrocarbons which contain four carbon atoms and may be saturated, monounsaturated or polyunsaturated. The main components of a crack-C4 stream are n-butane, isobutane, isobutene, n-butenes, butadienes.

Raffinate 1 is obtained from crack-C4 after (generally extractive) removal of the butadienes. Raffinate 1 is composed of about 42% isobutene, 26% 1-butene, 17% cis- and trans-2-butene, and also 0.3% 1,3-butadiene and 15% n-butane and isobutane. The exact composition can vary by source and also seasonally. The values reported are therefore merely typical but nonlimiting examples.

Raffinate II is a portion of the C$_4$ fraction which arises in naphtha cracking and consists essentially of the isomeric n-butenes, isobutane and n-butane after removal of isobutene from raffinate 1.

Raffinate III is a portion of the C$_4$ fraction which arises in naphtha cracking and consists essentially of the isomeric n-butenes and n-butane.

2-butene 99+%, mixture of cis and trans, Sigma Aldrich, catalogue number 36,335-9, LOT No. 14205MS The isobutene used has a purity of min. 99.9% (m/m). The manufacturer is Evonik Industries AG, Performance Materials.

Di-n-butene was also referred to as follows: dibutene, DNB or DnB.

Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which have to be removed by distillation after the reaction.

One process practised in industry for oligomerization of C4 olefins is called the "OCTOL process".

Within the patent literature, DE102008007081A1, for example, describes an oligomerization based on the OCTOL process. EP1029839A1 is concerned with the fractionation of the C8 olefins formed in the OCTOL process.

Technical di-n-butene consists generally to an extent of 5% to 30% of n-octenes, 45% to 75% of 3-methylheptenes, and to an extent of 10% to 35% of 3,4-dimethylhexenes. Preferred streams contain 10% to 20% n-octenes, 55% to 65% 3-methylheptenes, and 15% to 25% 3,4-dimethylhexenes.

para-Toluenesulphonic acid was abbreviated as follows: pTSA, PTSA or p-TSA.

PTSA in this text always refers to para-toluenesulphonic acid monohydrate.

General Method for Performance of the High-Pressure Experiments:

General Experiment Description for Reactions in Batchwise Mode:

The appropriate amounts of substrate, palladium salt, acid and alcohol are mixed under argon in a 50 ml Schlenk vessel while stirring with a magnetic stirrer.

A 100 ml steel autoclave from Parr provided with a gas inlet and a gas outlet valve, a digital pressure transducer, a temperature sensor and a ball valve, and an installed capillary for sampling, is freed of oxygen by means of vacuum and argon purging three times. Subsequently, the reaction solution from the Schlenk flask is introduced by means of a capillary into the autoclave in an argon counterflow through the ball valve. Subsequently, either the appropriate amount of CO is injected at room temperature and then the autoclave is heated up to reaction temperature (reactions that are not run under constant pressure) or the autoclave is first heated up to reaction temperature and then the CO is injected by means of a burette connected to the autoclave by means of a pressure reducer. This burette is then filled with CO to about 100 bar and, during the reaction, supplies the CO required at a constant pressure. This burette has a dead volume of about 30 ml and is provided with a digital pressure transducer. Then the reaction is conducted at the required temperature for the required time while stirring. In the course of this, by means of software (Specview from SpecView Corporation) and a Parr 4870 process controller and a 4875 power controller, data for the pressure variation in the autoclave and in the gas burette are recorded. These data are used to generate Excel tables, which are used at a later stage to create diagrams which show gas consumptions and hence conversions over time. If required, via the capillary, the GC samples are collected and analysed. For this purpose, a suitable exact amount (2-10 ml) of isooctane as internal standard is also added to the Schlenk vessel. These also give information about the course of the reaction. At the end of the reaction, the autoclave is cooled down to room temperature, the pressure is cautiously released, isooctane is added if necessary as internal standard, and a GC analysis or, in the case of new products, a GC-MS analysis is conducted as well.

General Experimental Method for Autoclave Experiments in Glass Vials:

A 300 ml Parr reactor is used. Matched to this is an aluminium block of corresponding dimensions which has been manufactured in-house and which is suitable for heating by means of a conventional magnetic stirrer, for example from Heidolph. For the inside of the autoclave, a round metal plate of thickness about 1.5 cm was manufactured, containing 6 holes corresponding to the external diameter of the glass vials. Matching these glass vials, they are equipped with small magnetic stirrers. These glass vials are provided with screw caps and suitable septa and charged, using a special apparatus manufactured by glass blowers, under argon with the appropriate reactants, solvents and catalysts and additives. For this purpose, 6 vessels are filled at the same time; this enables the performance of 6 reactions at the same temperature and the same pressure in one experiment. Then these glass vessels are closed with screw caps and septa, and a small syringe cannula of suitable size is used to puncture each of the septa. This enables gas exchange later in the reaction. These vials are then placed in the metal plate and these are transferred into the autoclave under argon. The autoclave is purged with CO and filled at room temperature with the CO pressure intended. Then, by means of the magnetic stirrer, under magnetic stirring, the autoclave is heated to reaction temperature and the reaction is conducted for the appropriate period. Subsequently, the autoclave is cooled down to room temperature and the pressure is slowly released. Subsequently, the autoclave is purged with nitrogen. The vials are taken from the autoclave, and a defined amount of a suitable standard is added. A GC analysis is effected, the results of which are used to determine yields and selectivities.

General Method for Experiments in the 12-Vial Autoclaves (600 ml Parr Autoclave):

Baked-out glass vials are each initially charged with di-n-butene (DNB) and methanol, and a solution of Pd(acac)$_2$ (0.5 mg, 0.0016 mmol) and ligand (0.0064 mmol) in 0.2 ml of methanol is added, as is $H_2SO_4$ (solution: 1 ml of $H_2SO_4$ in 50 ml MeOH). In the autoclave, the mixtures are purged twice with 10 bar of CO, CO is injected to the desired pressure, and the mixtures are stirred at the desired temperature for 20 h. After the reaction has ended, isooctane (internal standard) and 1 ml of EtOAc are added in each case. The organic phase is analysed by GC.

The yields of the reactions are determined by means of GC (isooctane as internal standard).

Analysis:

GC analysis of the products from ethene: For the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1. Retention time of methyl propionate: 6.158 min GC analysis of the products from 2-butene:

For the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1.

Retention time for iso-C5 esters: 12.118 min

Retention time for n-C5 esters: 13.807 min

GC analysis of the products from raffinate 1: For the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1.

Retention time for MTBE: 5.067 min

Retention time for iso-C5 esters: 12.118 min

Retention time for n-C5 esters: 13.807 min

GC analysis of the products from crack-C4: Agilent 7890A chromatograph with a 30 m HP5 column, temperature profile: 35° C., 10 min; 10° C./min to 200° C., 16.5 min; the injection volume is 1 µl with a split of 50:1.

Retention time for methyl pentanoate: 13.842 min

Retention time for methyl pent-3-enoate: 14.344 min, 14.533 min

Retention time for dimethyl adipate: 21.404 min

GC analysis of the products from isobutene:

Agilent 7890A chromatograph with a 30 m HP5 column, temperature profile: 35° C., 10 min; 10° C./min to 200° C., 16.5 min; the injection volume is 1 µl with a split of 50:1.

Retention time for MTBE: 5.045 min

Retention time for C5 esters: 12.105 min

GC analysis of the products from tetramethylethene: For the GC analysis, an Agilent 7890A gas chromatograph having a 30 m HP column is used. Temperature profile: 35° C., 10 min; 10° C./min to 200° C., 16.5 min; the injection volume is 1 µl with a split of 50:1.

Retention time for tetramethylethylene and products: 7.436 min

Retention time for the ether: 11.391 min

Retention time for methyl 3,4-dimethylpentanoate: 17.269 min

GC analysis of C-5 mixture and products: For the GC analysis, an Agilent 7890A gas chromatograph having a 30 m HP column is used. Temperature profile: 35° C., 10 min; 10° C./min to 200° C., 16.5 min; the injection volume is 1 μl with a split of 50:1.

Retention times for the C5 olefins: 4.498, 4.437, 4.533, 4.533, 5.465, 5.793 min;

Retention times for the C6 methyl esters and their isomers: 14.547-16.362 min (main peak: 16.362 min)

GC analysis of di-n-butene: For the GC analysis, an Agilent 7890A gas chromatograph having a 30 m HP5 column is used. Temperature profile: 35° C., 10 min; 10° C./min to 200° C.; the injection volume is 1 μl with a split of 50:1.

Retention times for di-n-butene and products: 10.784-13.502 min

The esters formed from di-n-butene are referred to hereinafter as MINO (methyl isononanoate).

Retention times for ether products of unknown isomer distribution: 15.312, 17.042, 17.244, 17.417 min Retention time for iso-C9 esters 19.502-20.439 min (main peak: 19.990 min)

Retention time for n-C9 esters: 20.669, 20.730, 20.884, 21.266 min.

GC analysis of the products from 1,3-butadiene: For the GC analysis, an Agilent 7890A gas chromatograph having a 30 m HP column is used. Temperature profile: 35° C., 10 min; 10° C./min to 200° C., 16.5 min; the injection volume is 1 μl with a split of 50:1. Retention time for methyl pent-3-enoate: 14.430 min, retention time for dimethyl adipate: 21.404 min.

GC analysis for methyl tert-butyl ether (MTBE) and products: Agilent 7890A chromatograph with a 30 m HP5 column, temperature profile: 35° C., 10 min; 10° C./min to 200° C., 16.5 min; the injection volume is 1 μl with a split of 50:1.

Retention time of methyl 3-methylbutanoate: 12.070 min

Retention time of MTBE: 5.067 min

GC analysis for aromatic alcohols and products: Agilent 7890A chromatograph with a 30 m HP5 column, temperature profile: 35° C., 10 min; 10° C./min to 200° C., 16.5 min; the injection volume is 1 μl with a split of 50:1.

Retention time: 21.197 min.

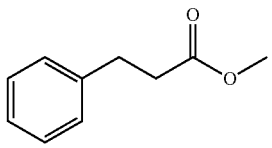

Retention time: 21.988 min.

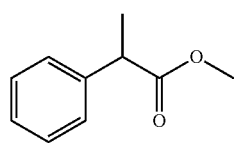

GC analysis for secondary alcohols and products: Agilent 7890A chromatograph with a 30 m HP5 column, temperature profile: 35° C., 10 min; 10° C./min to 200° C., 16.5 min; the injection volume is 1 μl with a split of 50:1.

Retention time for 3,3-dimethylbutan-2-ol: 10.975

Retention time for methyl 2,3,3-trimethylbutanoate: 15.312 min,

Retention time of methyl 4,4-dimethylpentanoate: 17.482 min.

GC analysis for tert-butanol and products: Agilent 7890A chromatograph with a 30 m HP5 column, temperature profile: 35° C., 10 min; 10° C./min to 200° C., 16.5 min; the injection volume is 1 μl with a split of 50:1.

Retention time of tert-butanol: 4.631

Retention time of methyl 3-methylbutanoate: 12.063 min.

GC analysis for methyl oleate and products:

For the GC analysis, an Agilent 7890A gas chromatograph having a 30 m HP column is used. Temperature profile: 50° C., 0 min; 8° C./min to 260° C., 15 min; the injection volume is 1 μl with a split of 50:1. Retention time for methyl oleate: 23.823 min, retention time for dimethyl nonadecane-1,19-dioate: 28.807 min, retention time for dimethyl nonadecane-1,X-dioate: 27.058 min main peak, 27.058, min, 27.206 min, 27.906 min, 28.831 min (secondary peaks). The position X is analytically undetermined.

Methanol Analysis

Methanol was pretreated in a solvent drying system: PureSolv MD Solvent Purification System, from Innovative Technology Inc. One Industrial Way, Amesbury Mass. 01013

Water Values:

Determined by Karl Fischer titration: TitraLab 580-TIM580, from Radiometer Analytical SAS (Karl Fischer titration), water content: measurement ranges, 0.1%-100% w/w, measured water content: 0.13889%

The following were used:

Technical grade methanol from Applichem: No. A2954, 5000, batch number: LOT: 3L005446 water content max. 1%

Methanol from Acros Organics (over molecular sieve): water content 0.005%, code number: 364390010, batch number: LOT 1370321

TON: turnover number, defined as moles of product per mole of catalyst metal

TOF: turnover frequency, defined as TON per unit time for the attainment of a particular conversion, e.g. 50%.

The n/iso ratio indicates the ratio of olefins converted terminally to esters to olefins converted internally to esters.

The n selectivities reported hereinafter relate to the proportion of terminal methoxycarbonylation based on the overall yield of methoxycarbonylation products.

Methoxycarbonylation of Ethene with Ligands 3 and 8 at 80° C. and 40 Bar

The ligand 8 was tested in comparison with the DTBPMB ligand 3 at 80° C. and 40 bar of CO. The results are shown in FIG. 1 (FIG. 1: methoxycarbonylation of ethene with 3 and 8 at 80° C. and 40 bar of CO).

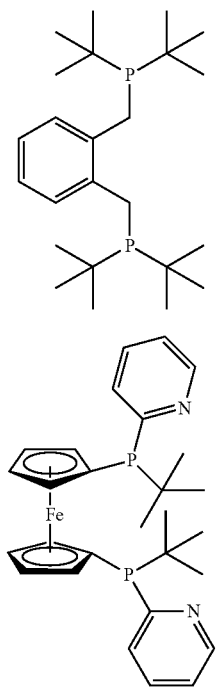

It can be seen very clearly in FIG. 1 that the catalyst comprising ligand 8 is much more active at 80° C. than that comprising DTBPMB (ligand 3), by about a factor of 5-6. While the system comprising 8 is ready after only 10 minutes, 3 needs about 60-70 minutes. Both attain the highest possible chemoselectivity (100%) for methyl propionate. Thus, the ligand according to the invention shows a distinct improvement over the system from the prior art.

Therefore, the system comprising 8 was studied in more detail and reactions were conducted at 60° C. and 20 bar (important industrial pressure level) of CO, with the pressure of 20 bar being kept constant.

Methoxycarbonylation of Ethene with Ligands 3 and 8 at 60° C. and 20 Bar:

3 (comparative example): A 100 ml steel autoclave is charged under argon with [Pd(acac)$_2$] (6.53 mg, 0.04 mol %), and the appropriate ligand 3 (33 mg, 0.16 mol %) and p-toluenesulphonic acid (PTSA, 61 mg, 0.6 mol %). Subsequently, MeOH (20 ml) and ethene of 3.0 purity (1.5 g, 53 mmol) are added. The autoclave is heated to 60° C. and then CO is injected up to a total pressure of 20 bar. This pressure is kept constant at 20 bar by metering in CO from a pressurized reservoir. The reaction is conducted for one hour and the gas consumption in the pressurized reservoir is measured. Subsequently, the autoclave is cooled down and the pressure is slowly released. The contents of the autoclave are transferred into a Schlenk vessel, and 5 ml of isooctane are added as internal standard. The yield was determined by means of GC analysis (100% yield). The TOF at 50% yield is 758 h$^{-1}$.

8: A 100 ml steel autoclave is charged under argon with [Pd(acac)$_2$] (6.53 mg, 0.04 mol %), and the appropriate ligand 8 (44 mg, 0.16 mol %) and p-toluenesulphonic acid (PTSA, 61 mg, 0.6 mol %). Subsequently, MeOH (20 ml) and ethene of 3.0 purity (1.5 g, 53 mmol) are added. The autoclave is heated to 60° C. and then CO is injected up to a total pressure of 20 bar. This pressure is kept constant at 20 bar by metering in CO from a pressurized reservoir. The reaction is conducted for one hour and the gas consumption in the pressurized reservoir is measured. Subsequently, the autoclave is cooled down and the pressure is slowly released. The contents of the autoclave are transferred into a Schlenk vessel, and 5 ml of isooctane are added as internal standard. The yield was determined by means of GC analysis (100% yield). The TOF at 50% yield is 3213 h$^{-1}$.

Figure 2:
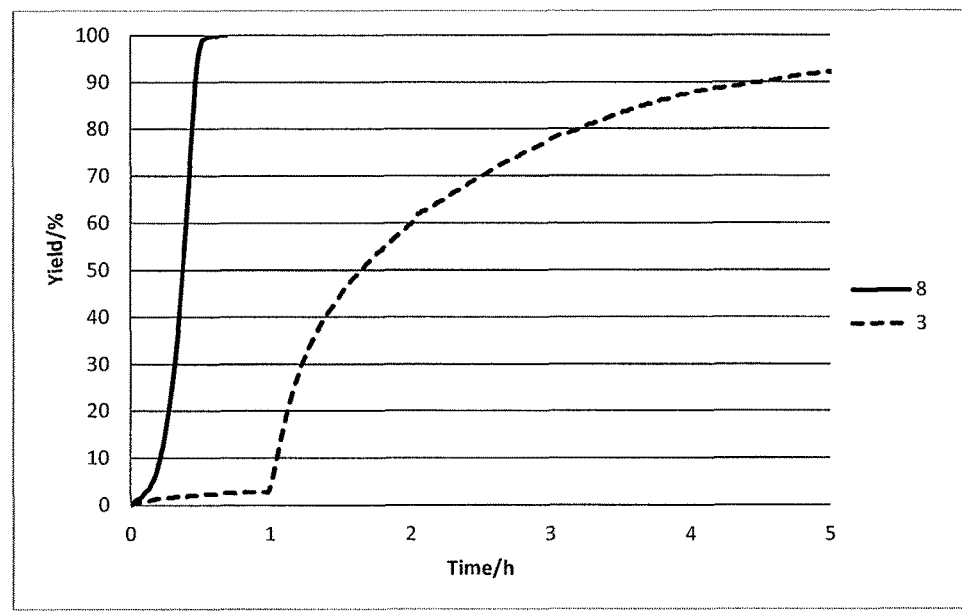
FIG. 2 methoxycarbonylation of ethene with 3 and 8 at 60° C. and 20 bar CO (constant pressure)

FIG. 2 shows the gas consumption from a pressurized reservoir. The reaction was started with the injection of CO at 60° C. (FIG. 2: methoxycarbonylation of ethene with 3 and 8 at 60° C. and 20 bar of CO (constant pressure)).

Here too, it is found that 8 conducts the reaction much more quickly and without a pre-formation phase. This is therefore a much quicker and highly selective catalyst system having distinct advantages over the prior art (ligand 3).

Alkoxycarbonylation (Comparative Experiment)

Scheme 10: Alkoxycarbonylation of ethene with ligand 59

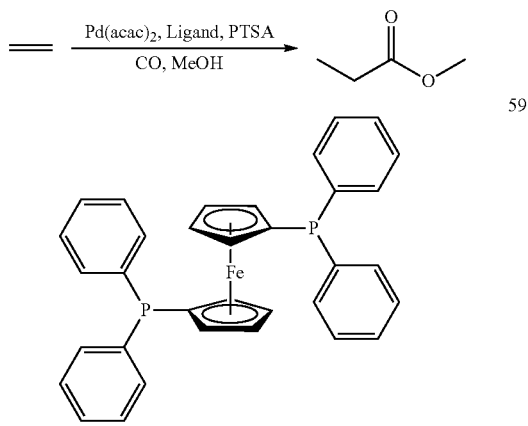

Ligand 59:

Ligand 59, 1,1'-bis(diphenylphosphino)ferrocene, is commercially available.

A 100 ml steel autoclave is charged with Pd(acac)$_2$ (6.52 mg, 0.04 mol %) and ligand 59 (47.9 mg, 0.16 mol %) and PTSA (61.1 mg, 0.6 mol %) and methanol (20 ml) under argon. Then 1.5 g (53.6 mmol) of ethylene (3.5 from Linde AG) are transferred into the autoclave. (Monitoring the mass of the autoclave). After the autoclave has been heated up to a reaction temperature of 80° C. (pressure about 10 bar), CO (30 bar) is injected at this temperature. At this temperature, the reaction is conducted for 20 hours. Then the autoclave is cooled down to room temperature and decompressed. The contents are transferred into a 50 ml Schlenk flask, and isooctane (internal standard, 5.0 ml) is added. The yield and selectivity were determined by means of GC analysis. (Yield: 54%).

Alkoxycarbonylation of Ethene with Various Alcohols

General procedure: A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of the appropriate alcohol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time.

The autoclave is cooled down to room temperature and the residual pressure is slowly released. The contents are transferred to a 50 ml Schlenk vessel, 5 ml of isooctane are added as internal standard, and the yield is determined by means of GC analysis.

GC analysis: For the GC analysis, an Agilent 7890A gas chromatograph having a 30 m HP column is used. Temperature profile: 35°, 10 min; 10°/min to 200°, 16.5 min; the injection volume 1 μl with a split of 50:1.

Scheme 11: Alkoxycarbonylation of ethene with various alcohols

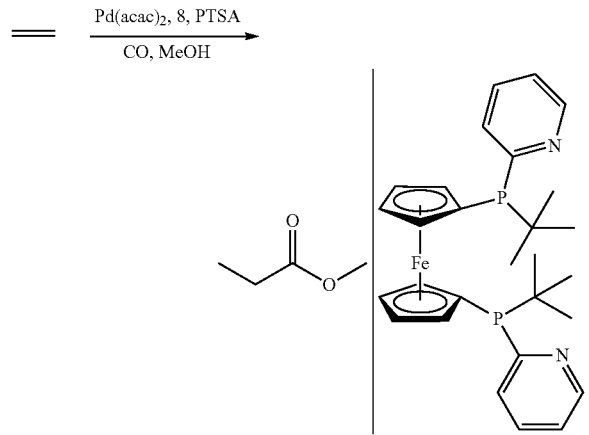

Methanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of methanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer in the autoclave and the Specview software from Parr Instruments and correlates to the plot of yield against time.

The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of methyl propionate. Retention time: 6.148 min Ethanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of ethanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of ethyl propionate. Retention time: 8.896 min 1-Propanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 1-propanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 1-propyl propionate. Retention time: 13.342 min 1-Butanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 1-butanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 1-butyl propionate. Retention time: 16.043 min 1-Pentanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 1-pentanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 1-pentyl propionate. Retention time: 17.949 min 1-Hexanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 1-hexanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 1-hexyl propionate. Retention time: 19.486 min 2-Propanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 2-propanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 2-propyl propionate. Retention time: 11.212 min t-Butanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of t-butanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 47% of t-butyl propionate. Retention time: 12.625 min 3-Pentanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of 3-pentanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of 3-pentyl propionate. Retention time: 16.648 min Cyclohexanol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of cyclohexanol are added under argon. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are transferred to a 50 ml Schlenk vessel, 5 ml of isooctane are added as internal standard, and the yield is determined by means of GC analysis. At the end of the reaction, it is 100% of cyclohexyl propionate. Retention time: 19.938 min Phenol:

A 100 ml steel autoclave is charged under argon with Pd(acac)$_2$ (6.52 mg, 0.04 mol %), 8 (44.3 mg, 0.16 mol %) and PTSA (61.1 mg, 0.6 mol %). 20 ml of phenol are added under argon. Phenol was added in solid form without solvent. The melting point of phenol is 40.5° C. All components should therefore be dissolved at 80° C. Then 1.5 g of ethene (53.6 mmol) are transferred into the autoclave (monitoring by mass). The autoclave is heated to 80° C. (the pressure is now about 10 bar). At this temperature, CO is injected to 30 bar and the reaction is conducted for 20 h while stirring. The gas consumption is measured with a pressure transducer and the Specview software from Parr Instruments and correlates to the plot of yield against time. The autoclave is cooled down to room temperature and the residual pressure is slowly released. The contents are trans-ferred to a 50 ml Schlenk vessel, 5 ml of isooctane are added as internal standard, and the yield is determined by means of GC analysis. At the end of the reaction, it is 46% of phenyl propionate. Retention time: 20.260 min The results are shown in FIG. 3.

Figure 3:
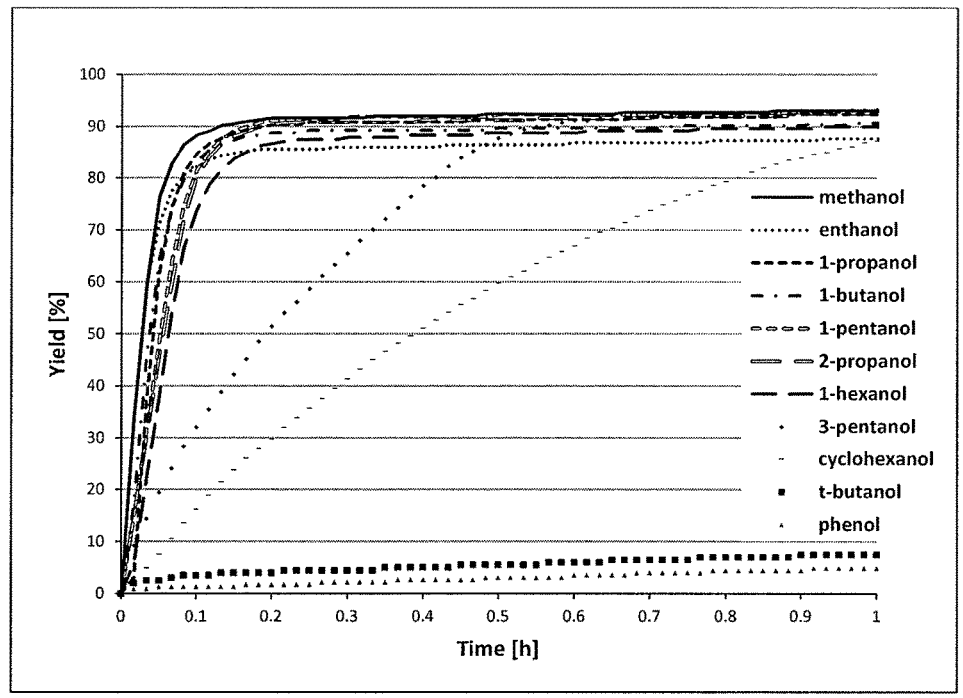
FIG. 3 alcohol variation in the methoxycarbonylation of ethene with ligand 8 at 80° C. and CO pressure 30 bar FIG. 4 methoxycarbonylation experiments on propene, 1-butene and 2-butene at 100° C. and 40 bar with ligand 8.

FIG. 3: Alcohol variation in the methoxycarbonylation of ethene with ligand 8 at 80° C. and CO pressure 30 bar As is clearly apparent, it is possible to use not only methanol in the alkoxylation, but it is likewise also possible to use a multitude of other alcohols. The corresponding products can be obtained in good to very good yields (in some cases quantitatively).

Conversion of 8 with Propene

Scheme 12: Conversion of propene with 8

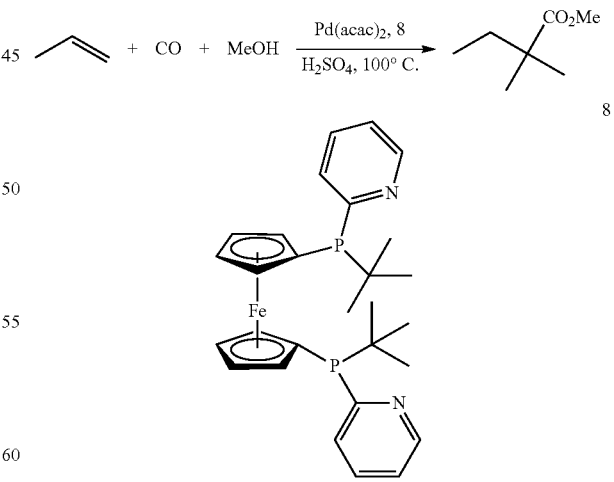

A 100 ml steel autoclave is charged under argon with Pd(acac)$_2$ (17.5 mg, 0.04 mol %), 8 (119 mg, 0.16 mol %), MeOH (15 ml) and [98% H$_2$SO$_4$] (38 µl, 0.5 mol %). Then the autoclave is cooled down with dry ice. Propene (6.06 g, 144 mmol) was condensed into another, separate cylinder (75 ml, monitoring by mass). This defined amount was then condensed into the autoclave. Then CO is injected into the autoclave to 40 bar at room temperature. The reaction is conducted at 100° C. for 30 minutes. After the reaction, the autoclave is cooled down to room temperature and the pressure is released. 8.5 ml of isooctane are added to the solution as an internal standard. The yield and selectivity were determined by means of GC analysis. (Yield: >99%, n/iso: 77:23).

Conversion of 1-Butene with 8

Scheme 13: Conversion of 1-butene with 8

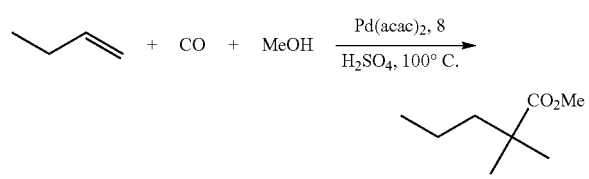

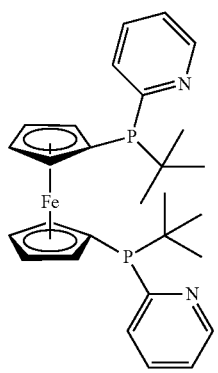

A 100 ml steel autoclave is charged under argon with Pd(acac)$_2$ (17.5 mg, 0.04 mol %), 8 (119 mg, 0.16 mol %), MeOH (15 ml) and [98% H$_2$SO$_4$] (38 µl, 0.5 mol %). Then the autoclave is cooled down with dry ice. 1-Butene (8.04 g, 144 mmol) was condensed into another, separate cylinder (75 ml, monitoring by mass). This defined amount was then condensed into the autoclave. Then CO is injected into the autoclave to 40 bar at room temperature. The reaction is conducted at 100° C. for 60 minutes. After the reaction, the autoclave is cooled down to room temperature and the pressure is released. 8.5 ml of isooctane are added to the solution as an internal standard. The yield and selectivity were determined by means of GC analysis. (Yield: >99%, n/iso: 80:20).

Conversion of 2-Butene with 8

Scheme 14: Conversion of 2-butene with 8

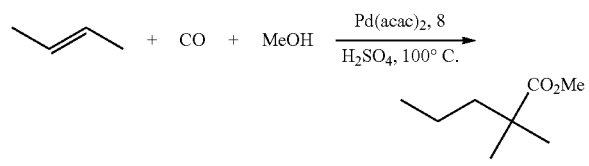

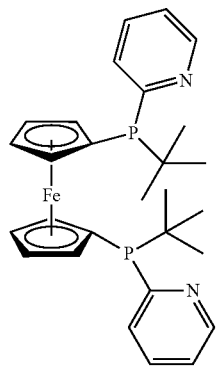

A 100 ml steel autoclave is charged under argon with Pd(acac)$_2$ (17.5 mg, 0.04 mol %), 8 (119 mg, 0.16 mol %), MeOH (15 ml) and [98% H$_2$SO$_4$] (38 µl, 0.5 mol %). Then the autoclave is cooled down with dry ice. 2-Butene (8.04 g, 144 mmol) was condensed into another, separate cylinder (75 ml, monitoring by mass). This defined amount was then condensed into the autoclave. Then CO is injected into the autoclave to 40 bar at room temperature. The reaction is conducted at 100° C. for 60 minutes. After the reaction, the autoclave is cooled down to room temperature and the pressure is released. 8.5 ml of isooctane are added to the solution as an internal standard. The yield and selectivity were determined by means of GC analysis. (Yield: >99%, n/iso: 75:25).

Figure 4:
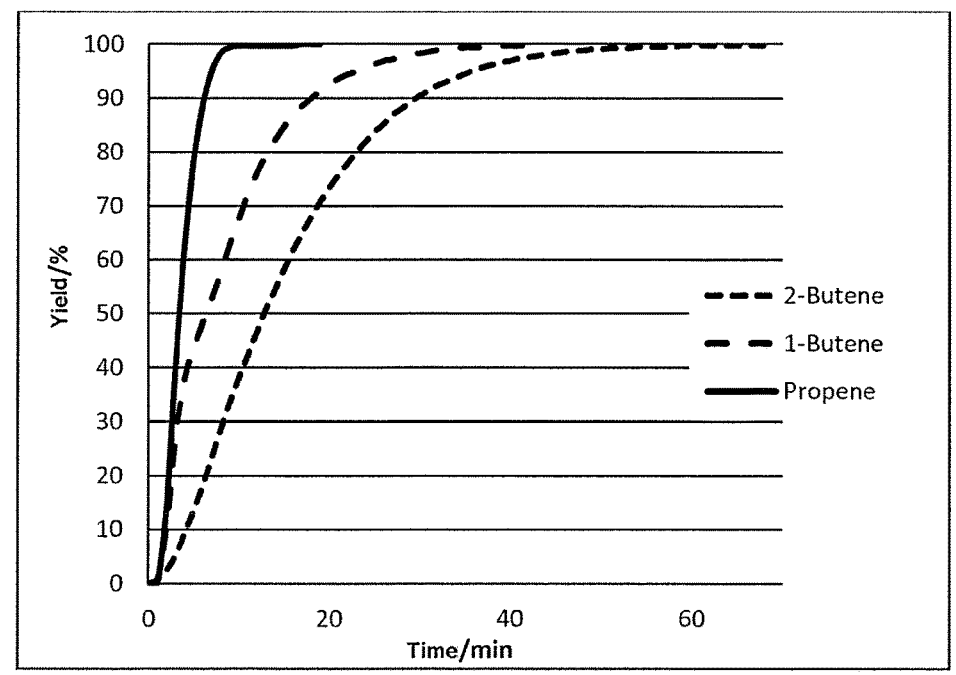

The results are shown in FIG. 4. This figure shows the yield profile of the abovementioned reactions, which was calculated by conversion from the gas consumption curve. The curve was fitted using the yield determined by gas chromatography on completion of reaction.

FIG. 4: Methoxycarbonylation experiments on propene, 1-butene and 2-butene at 100° C. and 40 bar with ligand 8.

As can be inferred from FIG. 4, the conversion rates of the olefins fall with rising chain length. The conversion rate is higher for terminal olefins than for the olefins with an internal double bond. While propene has been fully converted within less than 10 minutes, about 40 minutes are needed for 1-butene and almost 60 minutes for 2-butene for a complete conversion (100% yield).

Conversion of Raffinate 1 with Compound 8

Technical mixtures were also tested, including what is called raffinate 1. Raffinate 1 is composed of 42% isobutene, 26% 1-butene, 17% cis- and trans-2-butene, and also 0.3% 1,3-butadiene and 15% n-butane and isobutane.

Method: A 100 ml steel autoclave was charged under an argon atmosphere with [Pd(acac)$_2$] (17.4 mg), 8 (118.9 mg) and H$_2$SO$_4$ (70.6 mg). Methanol (15 ml) was added under an Ar atmosphere. The autoclave was cooled with dry ice. Thereafter, 8.2 g of raffinate 1 were condensed into a separate cylinder (75 ml, monitoring by mass) and this defined amount of substrate was condensed into the cooled autoclave. Thereafter, the autoclave was pressurized with 60 bar of CO at room temperature. The reaction was conducted at 100° C. for 20 h. Thereafter, the contents were transferred into a 50 ml Schlenk flask, and isooctane was added as internal standard. Yield and selectivity were determined by means of GC analysis.

Result: C5-Ester: 9.7 g, n/iso 37/63, MTBE: 2.0 g.

Scheme 15: Reaction of raffinate 1 with ligand 8

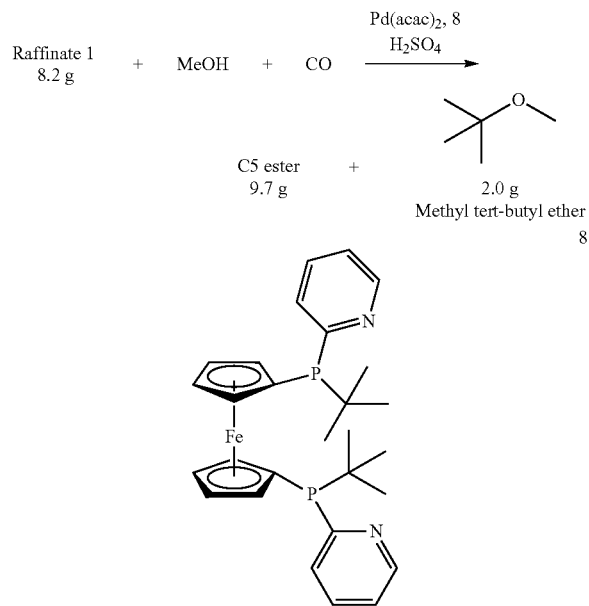

Figure 5:
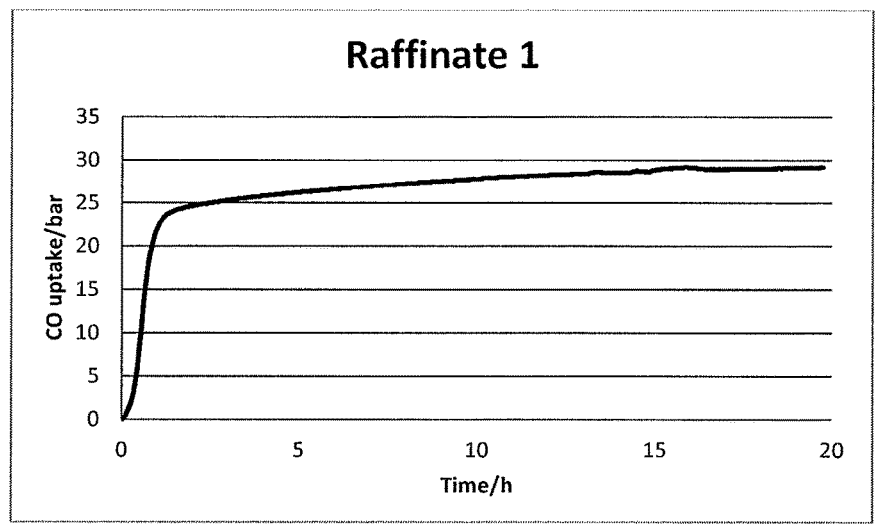
FIG. 5 methoxycarbonylation of raffinate 1 with ligand 8 at 100° C. and CO pressure 60 bar.

The results are also shown in FIG. 5.

FIG. 5: Methoxycarbonylation of raffinate 1 with ligand 8 at 100° C. and CO pressure 60 bar.

It has thus been shown that mixtures of industrial relevance too, such as raffinate 1 here, can be converted with the ligand 8 according to the invention.

Raffinate 1 with Sampling

In addition, raffinate 1 was converted with ligand 8.

Scheme 16: Methoxycarbonylation of raffinate 1

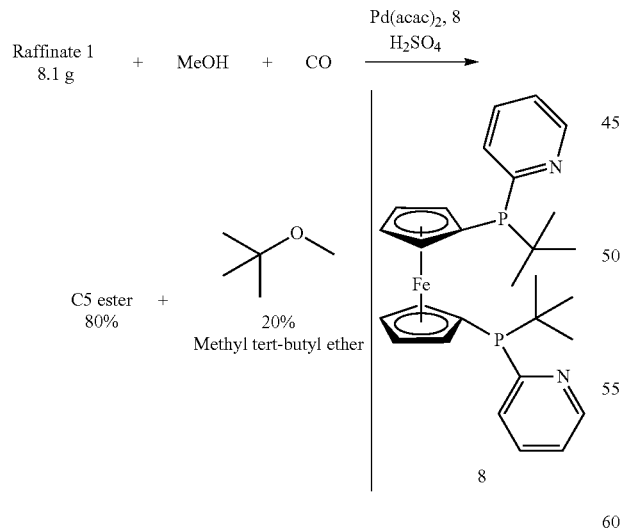

General procedure: A 100 ml steel autoclave is charged under argon with [Pd(acac)$_2$] (17.4 mg), 8 (118.9 mg) and H$_2$SO$_4$ (70.6 mg). Then 15 ml of MeOH and 10 ml of isooctane as an internal standard are added. Then the autoclave is cooled down to −78° C. with dry ice. Raffinate 1 (8.1 g) is condensed into a separate 75 ml pressure cylinder (monitoring by mass). This defined mass is then condensed into the autoclave. The autoclave is charged with 50 bar of CO at room temperature. The autoclave is heated to 100° C. and stirred at this temperature for 20 h. During this period, 16 samples are taken from the autoclave by means of an HPLC valve and an internal capillary. The yield and selectivity are determined by means of GC analysis. GC analysis: For the GC analysis, an Agilent 7890A gas chromatograph having a 30 m HP column is used. Temperature profile: 35°, 10 min; 10°/min to 200°, 16.5 min; the injection volume is 1 μl with a split of 50:1.

Figure 6:
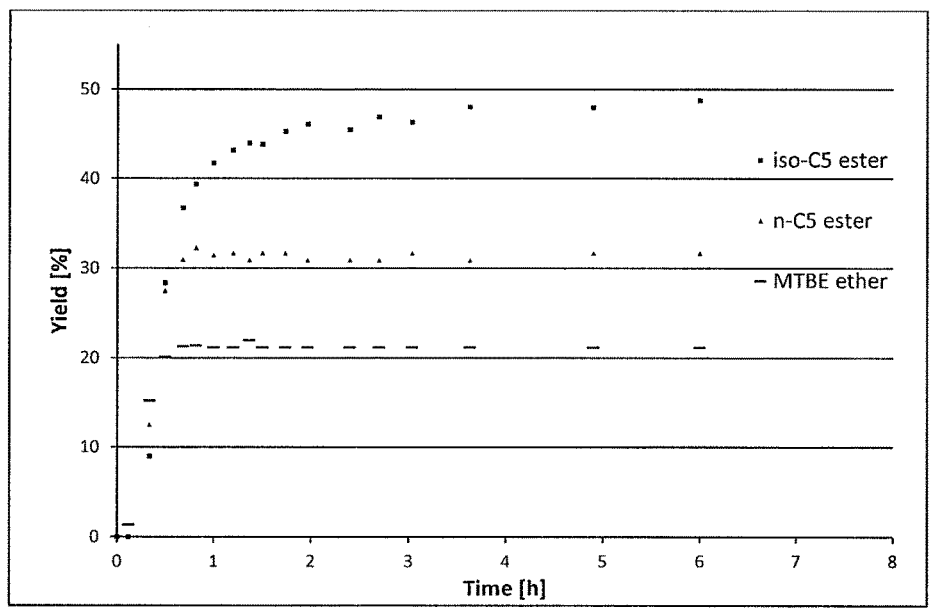
FIG. 6 methoxycarbonylation of raffinate 1 at 100° C. and 50 bar with ligand 8.

Retention time for MTBE: 5.067 min
Retention time for iso-C5 esters: 12.118 min
Retention time for n-C5 esters: 13.807 min The results are shown in FIG. 6.

FIG. 6: Methoxycarbonylation of raffinate 1 at 100° C. and 50 bar with ligand 8. At the end of the reaction, 80% C5 ester and 20% methyl tert-butyl ether are present, based on the amount of olefins used.

Thus, the ligand 8 is of good suitability for the conversion of a feed of industrial relevance, raffinate 1.

FIG. 5 shows the gas uptake curve for the experiment without sampling which has run for 20 hours and has led to 9.7 g of C5 ester with an n/iso ratio of 37/63 and an MTBE content of 2.0 g. The experiment conducted in FIG. 6 leads to 32% n-C5 ester and 48% iso-C5 ester. This corresponds to an n/iso ratio of 33/67. The proportion by mass of methyl tert-butyl ether is 20%. FIG. 5 shows a proportion by mass of 17%. The two experiments thus give similar results. It is apparent from FIG. 5 that most of the reaction has already ended after about 1 hour. This too is in accordance with the experiment with sampling in FIG. 6.

Methoxycarbonylation of Isobutene with Ligand 3 and 8

Scheme 17: Methoxycarbonylation of isobutene with ligand 3 and 8

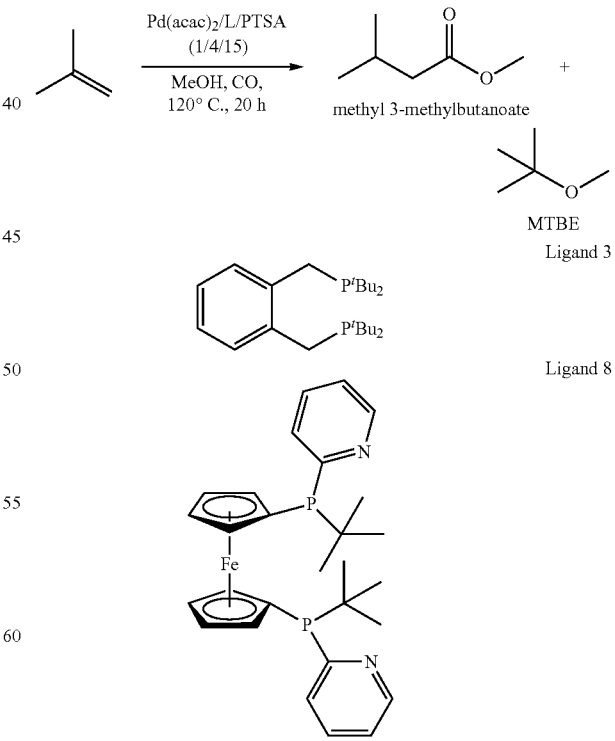

Ligand 3 (comparative example): A 100 ml steel autoclave is charged under argon with Pd(acac)$_2$ (4.9 mg), DTBPMB (25.3 mg), PTSA (45.6 mg) and MeOH (20 ml). Subsequently, the autoclave is cooled down with dry ice. In a separate pressure vessel, 2.5 g of isobutene (monitoring by mass) are condensed in. This defined mass is condensed into the autoclave. Then the autoclave is charged with CO to 40 bar at room temperature. The reaction is conducted at 120° C. for 20 hours. Subsequently, the autoclave is cooled down to room temperature and decompressed, the contents are transferred to a 50 ml Schlenk vessel, and isooctane (5 ml as internal standard) is added. A GC analysis is effected. (GC analysis (50% yield of methyl 3-methylbutanoate, 37% yield of MTBE).

Ligand 8: A 100 ml steel autoclave is charged under argon with Pd(acac)$_2$ (4.9 mg), 8 (33.1 mg), PTSA (45.6 mg) and MeOH (20 ml). Subsequently, the autoclave is cooled down with dry ice. In a separate pressure vessel, 2.5 g of isobutene (monitoring by mass) are condensed in. This defined mass is condensed into the autoclave. Then the autoclave is charged with CO to 40 bar at room temperature. The reaction is conducted at 120° C. for 20 hours. Subsequently, the autoclave is cooled down to room temperature and decompressed, the contents are transferred to a 50 ml Schlenk vessel, and isooctane (5 ml as internal standard) is added. A GC analysis is effected. (99% yield of methyl 3-methylbutanoate)

Testing of a Mixture of Propene, 1-Butene and 2-Butene

In addition, mixtures of reactants were also tested, i.e. mixtures which comprise different unsaturated compounds.

Method: A 100 ml steel autoclave was charged under an argon atmosphere with [Pd(acac)$_2$] (17.4 mg), 8 (118.9 mg) and H$_2$SO$_4$ (70.6 mg). Methanol (15 ml) was added under an Ar atmosphere. The autoclave was cooled with dry ice. Thereafter, 2.83 g, 2-butene 4.85 mg and propene (2.2 g) were condensed into three separate cylinders (75 ml, monitoring by mass) and these defined amounts of gas substrate were condensed into the cooled autoclave. Thereafter, the autoclave was pressurized with 60 bar of CO at room temperature. The reaction was conducted at 100° C. for 20 h. Thereafter, the contents were transferred into a 50 ml Schlenk flask, and isooctane was added as internal standard. Yield and selectivity were determined by means of GC analysis. (Yield: 100%, C4 esters: n/iso 79/21, C5 esters: n/iso: 75/25).

Scheme 18: Mixture of propane, 1-butene and 2-butene in the methoxycarbonylation with ligand 8

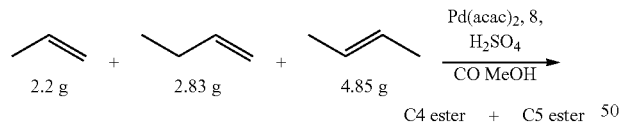

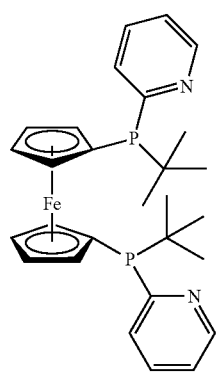

Figure 7:
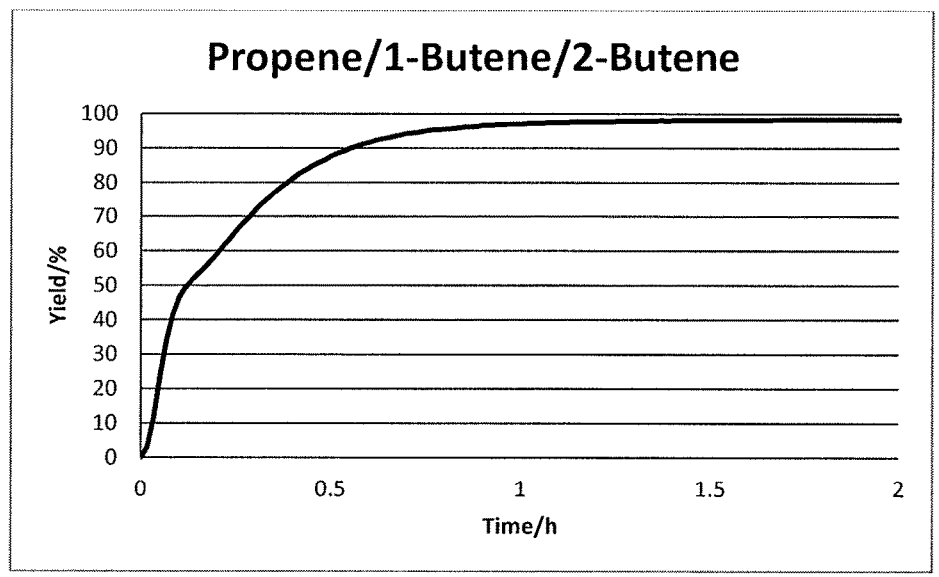
FIG. 7 methoxycarbonylation of a mixture of propene, 1-butene and 2-butene at 100° C. and 60 bar with ligand 8.

The results are shown in FIG. 7.

FIG. 7: Methoxycarbonylation of a mixture of propene, 1-butene and 2-butene at 100° C. and 60 bar with ligand 8.

As can be inferred from FIG. 7, nearly a full yield of the methoxycarbonylation products is achieved with the mixture of propene, 1-butene and 2-butene after a reaction time of about 1 hour.

Conversion of Tetramethylethylene with Various Ligands at Various Temperatures

Scheme 19: Conversion of tetramethylethylene with various ligands at various temperatures

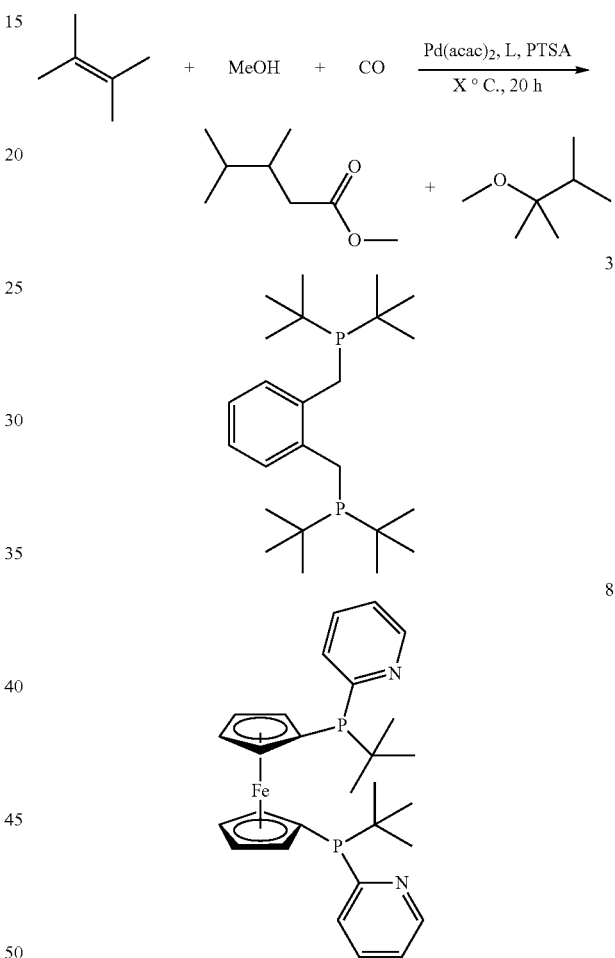

a) Reaction temperature: 100° C.

3 (comparative example): A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 3 (6.3 mg, 0.4 mol %), and a magnetic stirrer bar was added. Thereafter, 2 ml of the clear yellow solution and tetramethylethylene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 40%, no ester product yield; ether product yield 38%).

8: A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 8 (8.3 mg, 0.4 mol %), and a magnetic stirrer bar was added. Thereafter, 2 ml of the clear yellow solution and tetramethylethylene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 65%, ester product yield: 37%; ether product yield 27%).

b) Reaction temperature: 120° C.

3 (comparative example): A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 3 (6.3 mg, 0.4 mol %), and a magnetic stirrer bar was added. Thereafter, 2 ml of the clear yellow solution and tetramethylethylene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 54%, no ester product yield; ether product yield 52%).

8: A 25 ml Schlenk vessel was charged with [Pd(acac)$_2$] (4.87 mg, 0.1 mol %), p-toluenesulphonic acid (PTSA) (24.32 mg, 0.8 mol %) and MeOH (8 ml). A 4 ml vial was charged with 8 (8.3 mg, 0.4 mol %), and a magnetic stirrer bar was added. Thereafter, 2 ml of the clear yellow solution and tetramethylethylene (478 µl, 4 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane (200 µl) was added as internal GC standard. Yield and regioselectivity were determined by means of GC. (Conversion: 90%, ester product yield: 60%; ether product yield 28%).

Methoxycarbonylation of C5 Olefins

Procedure: A 100 ml steel autoclave is charged under argon with [Pd(acac)$_2$] (10.95 mg, 0.04 mol %), 8 (74.31 mg, 0.16 mol %) and H$_2$SO$_4$ (44.1 mg, 0.5 mol %). Subsequently, 10 ml of MeOH, 1-pentene (0.5 g), 2-pentene (2.21 g), 2-methyl-1-butene (1.27 g) and 2-methyl-2-butene (1.3 g) are added under argon. Then the autoclave is cooled down to −78° C. by means of dry ice. 1.1 g of 3-methyl-1-butene (1.1 g) are condensed into a separate pressure vessel (monitoring by mass) and this defined amount is condensed into the autoclave. Subsequently, the autoclave is charged with CO to 50 bar at room temperature. While stirring, the reaction is conducted at 100° C. for 20 h. Then the autoclave is cooled down to room temperature and the residual pressure is slowly released. The contents are transferred to a 50 ml Schlenk vessel, and 5 ml of isooctane are added as internal standard. The yield is determined by means of GC analysis. At the end of the reaction, it is 76% of C6 methyl esters.

GC analysis: For the GC analysis, an Agilent 7890A gas chromatograph having a 30 m HP column is used. Temperature profile: 35°, 10 min; 10°/min to 200°, 16.5 min; the injection volume 1 µl with a split of 50:1.

Retention times for the C6 methyl esters and their isomers: 14.547-16.362 min (main peak: 16.362 min)

Scheme 20: Mixture of various C5 olefins in the methoxycarbonylation

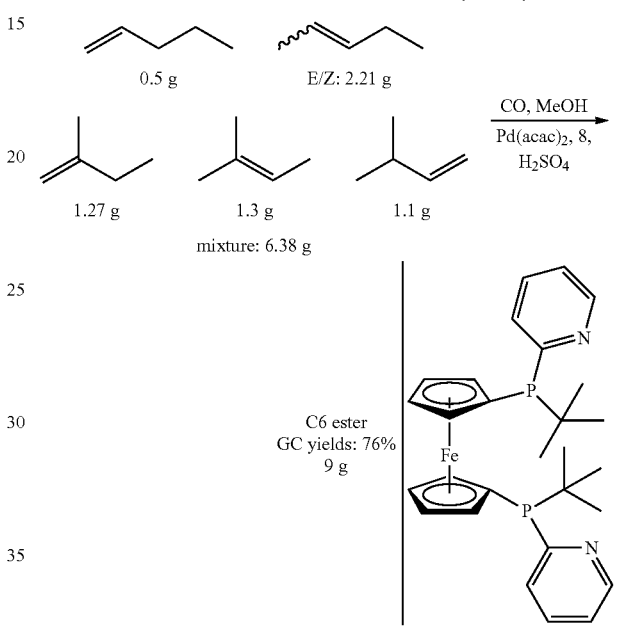

Figure 8:
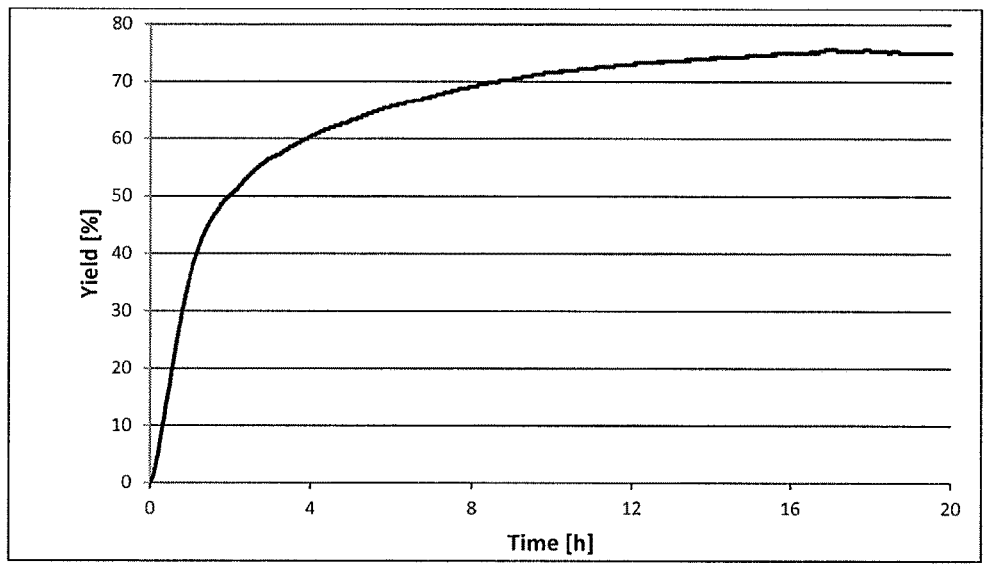
FIG. 8 methoxycarbonylation of a mixture of C5 olefins at 100° C. and CO pressure 50 bar with ligand 8.

The results are shown in FIG. 8.

FIG. 8: Methoxycarbonylation of a mixture of C5 olefins at 100° C. and CO pressure 50 bar with ligand 8.

As is clearly apparent, the corresponding C6 esters can be obtained as a mixture in good yields (distinctly >50%).

Conversion of Di-n-Butene with the Ligand 8

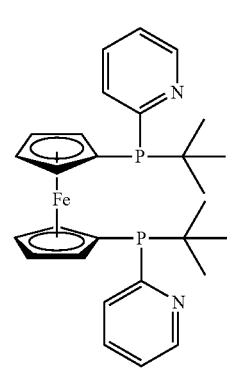

In addition, an experiment was conducted with constant pressure and gas consumption measurement with 8 at total pressure 20 bar.

Experimental example: A 100 ml steel autoclave is charged under argon with [Pd(acac)$_2$](5.85 mg, 0.04 mol %), and the appropriate ligand 8 (39.6 mg, 0.16 mol %) and p-toluenesulphonic acid (PTSA, 54.7 mg, 0.6 mol %). Subsequently, MeOH (30 ml) and di-n-butene (7.54 ml, 48 mmol) are added. The autoclave is heated to 120° C. and then CO is injected up to a total pressure of 20 bar. This pressure is kept constant at 20 bar by metering in CO from a pressurized reservoir. The reaction is conducted for 20 hours and the gas consumption in the pressurized reservoir is measured. Subsequently, the autoclave is cooled down and the pressure is slowly released. The contents of the autoclave are transferred into a Schlenk vessel, and 5 ml of isooctane are added as internal standard. The yield was determined by means of GC analysis (86% yield, n:iso=75:25).

Figure 9:
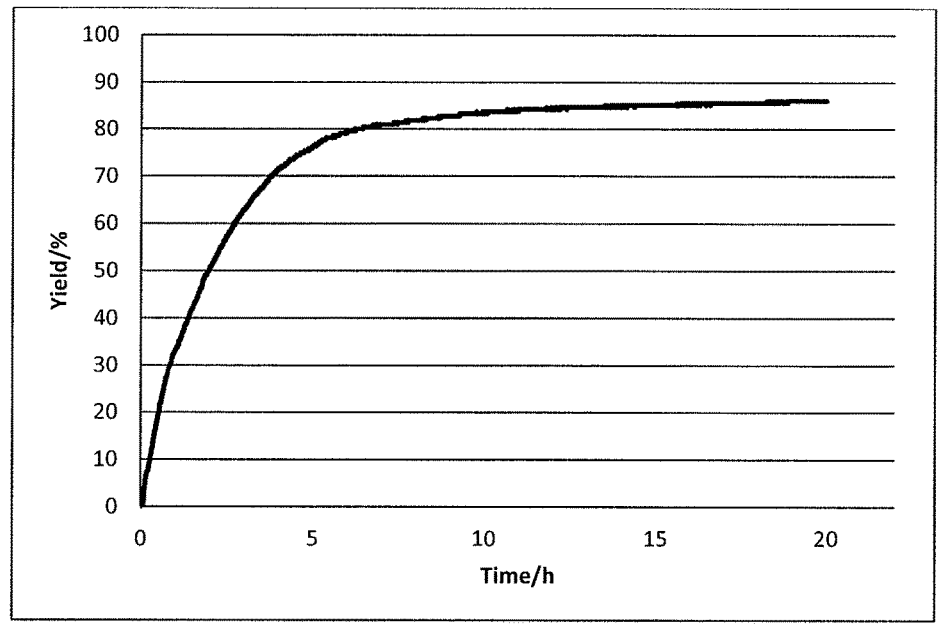
FIG. 9 methoxycarbonylation of di-n-butene with ligand 8 at 120° C. and 20 bar with constant CO pressure.

The results are shown in FIG. 9.

FIG. 9: Methoxycarbonylation of di-n-butene with ligand 8 at 120° C. and 20 bar with constant CO pressure After only 5 hours, with ligand 8, a yield of methyl isononanoate (MINO) of more than 80% is achieved; yield and n:iso ratio after 20 hours correspond to the experiment with ligand 8 at 120° C. and 40 bar under variable CO pressure (see above). A lower CO pressure of 20 bar during the reaction can thus be employed without loss of yield and selectivity.

Methoxycarbonylation of Di-n-Butene with Ligands 3 and 8

In order to have a good comparison of the ligands in the methoxycarbonylation of di-n-butene, experiments with gas consumption measurements were conducted.

Scheme 21: Testing of various ligands in the methoxycarbonylation of di-n-butene

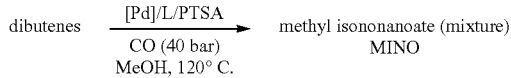

3 (comparative example): A 100 ml steel autoclave is charged under argon with [Pd(acac)$_2$](5.85 mg, 0.04 mol %) and 3 (30.3 mg, 0.16 mol %). Subsequently, MeOH (30 ml) and di-n-butene (7.54 ml, 48 mmol) and PTSA (54.7 mg, 0.6 mol %) are added. The autoclave is charged at room temperature with CO of purity 4.7 to 40 bar and the reaction is conducted at 120° C. for 20 hours. Subsequently, the autoclave is cooled down and the pressure is slowly released. The contents of the autoclave are transferred to a Schlenk flask. 5 ml of isooctane are added as internal standard and the yield and selectivity are determined by means of GC analysis (60% yield of MINO, n/iso: 93/7).

8: A 100 ml steel autoclave is charged under argon with [Pd(acac)$_2$] (5.85 mg, 0.04 mol %) and 8 (39.6 mg, 0.16 mol %). Subsequently, MeOH (30 ml) and di-n-butene (7.54 ml, 48 mmol) and PTSA (54.7 mg, 0.6 mol %) are added. The autoclave is charged at room temperature with CO of purity 4.7 to 40 bar and the reaction is conducted at 120° C. for 20 hours. Subsequently, the autoclave is cooled down and the pressure is slowly released. The contents of the autoclave are transferred to a Schlenk flask. 5 ml of isooctane are added as internal standard and the yield and selectivity are determined by means of GC analysis (86% yield of MINO, n/iso: 75/25).

Figure 10:
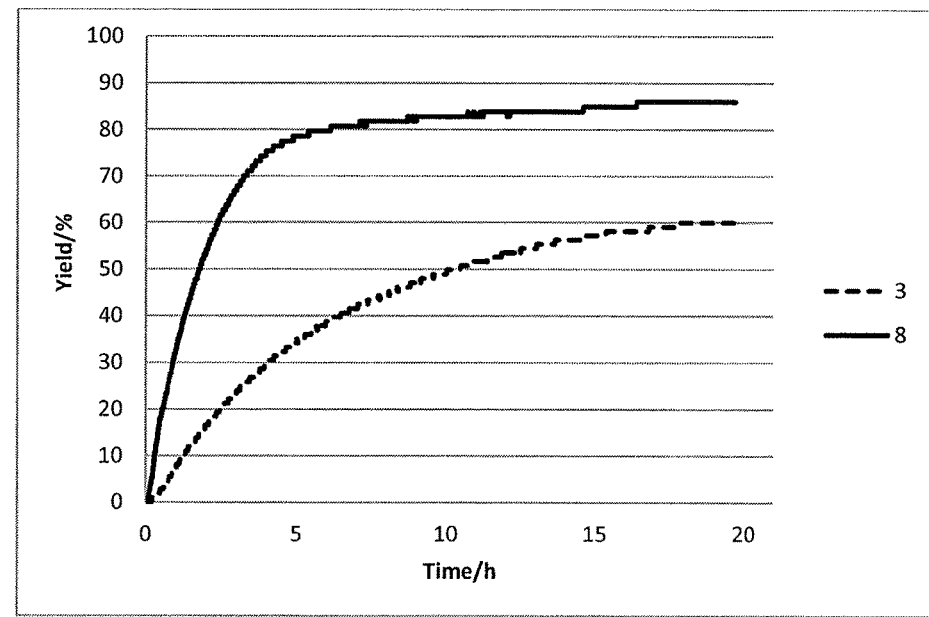
FIG. 10 methoxycarbonylation of di-n-butene with 3 and 8 at 120° C. and 40 bar CO.

FIG. 10 shows the gas consumption curves (or plot of yield against time) for the systems tested.

FIG. 10: Methoxycarbonylation of di-n-butene with 3 and 8 at 120° C. and 40 bar CO.

It is clearly apparent from the gas consumption measurements and the experimental examples that 8 is quicker than 3. Even though the n selectivity at 75% is lower than in the reactions with 3 as ligand, preference is given to ligand 8 with regard to possible industrial implementation and the very high space-time yield.

In addition, an experiment was conducted with constant pressure and gas consumption measurement with 8 at total pressure 20 bar.

Experimental example: A 100 ml steel autoclave is charged under argon with [Pd(acac)$_2$] (5.85 mg, 0.04 mol %), and the appropriate ligand 8 (39.6 mg, 0.16 mol %) and p-toluenesulphonic acid (PTSA, 54.7 mg, 0.6 mol %). Subsequently, MeOH (30 ml) and di-n-butene (7.54 ml, 48 mmol) are added. The autoclave is heated to 120° C. and then CO is injected up to a total pressure of 20 bar. This pressure is kept constant at 20 bar by metering in CO from a pressurized reservoir. The reaction is conducted for one hour and the gas consumption in the pressurized reservoir is measured. Subsequently, the autoclave is cooled down and the pressure is slowly released. The contents of the autoclave are transferred into a Schlenk vessel, and 5 ml of isooctane are added as internal standard. The yield was determined by means of GC analysis (86% yield, n:iso=75:25).

Figure 11:
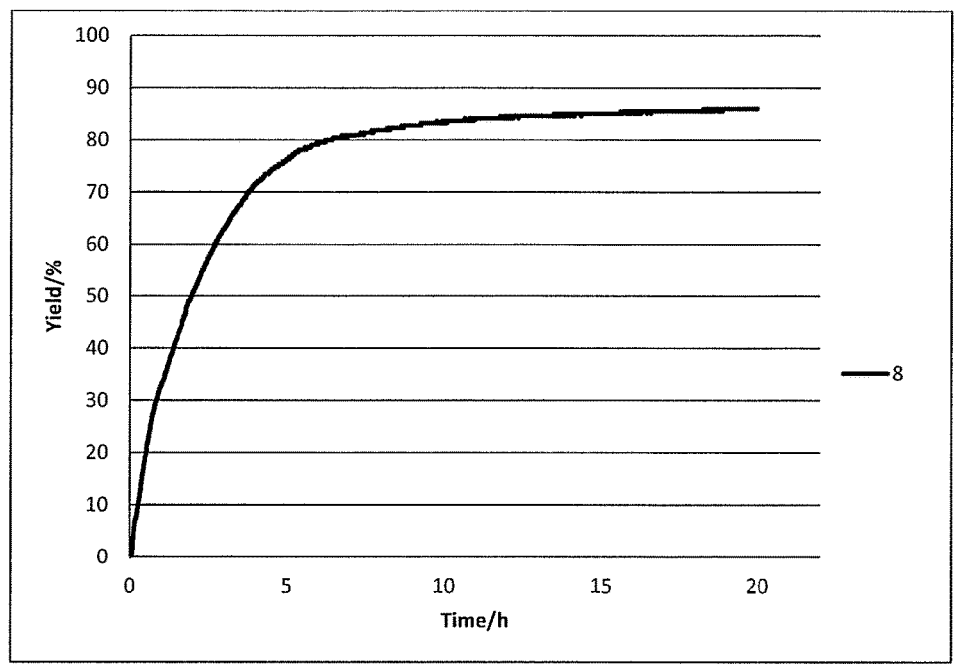
FIG. 11 yield curve for the methoxycarbonylation of di-n-butene with 8 as ligand at constant total pressure 20 bar and 120° C.

The results are shown in FIG. 11.

FIG. 11: Yield curve for the methoxycarbonylation of di-n-butene with 8 as ligand at constant total pressure 20 bar and 120° C.

An equal performance to that in the non-constant 40 bar CO experiment is found. This means that the methoxycarbonylation of di-n-butene with 8 as ligand is independent of the CO pressure over a certain CO pressure range, and industrially favourable lower pressures below 20 bar are achievable.

Conversion of Di-n-Butene with Further Ligands (Comparative Experiments in a 12-Well Autoclave)

The conversion of di-n-butene with the aid of various ligands was effected by the following method:

Method: A 50 ml Schlenk vessel was charged with [Pd(acac)$_2$] (3.9 mg, 0.04 mol %), MeSO$_3$H (methanesulphonic acid) (13 µl, 0.6 mol %) and MeOH (20 ml). A 4 ml vial was charged with ligand X (0.16 mol %), and a magnetic stirrer bar was added. Thereafter, 1.25 ml of the clear yellow stock solution and di-n-butene (315 µl, 2 mmol) were added with a syringe. The vial was placed into a sample holder which was in turn inserted into a 600 ml Parr autoclave under an argon atmosphere. After the autoclave had been purged three times with nitrogen, the CO pressure was adjusted to 40 bar. The reaction proceeded at 120° C. for 20 hours. On conclusion of the reaction, the autoclave was cooled down to room temperature and cautiously decompressed. Isooctane was added as internal GC standard. Yield and regioselectivity were determined by means of GC.

The results are summarized in Scheme 22 below:

Scheme 22: Catalysis results with a selection of ferrocenyl ligands

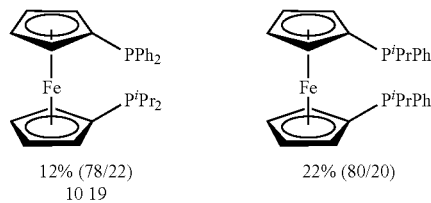

12% (78/22)      22% (80/20)
10 19

Determination of Space-Time Yield STY

The space-time yield (STY) is understood to mean the specific product output (amount of product formed in a reactor) of a reaction vessel (reactor) per unit space and time, for example t (tonnes) of product per cubic meter and unit time or kg per liter and second.

Method: A baked-out Schlenk flask is initially charged in each case with 1.6 mol % of PTSA (180 mg), 0.04 mol % of Pd(acac)$_2$ (7.5 mg) and 0.16 mol % of ligand 3 or 8. Then 6.26 ml (150 mmol) of methanol (technical grade) and 9.39 ml (60 mmol) of di-n-butene are added and the mixture is transferred to a 100 ml autoclave. The autoclave is then purged twice with CO at 10 bar, charged with CO to 6 bar and heated to 100° C. Then the autoclave is charged with CO to 12 bar by means of a gas burette and stirred at 100° C. under constant CO pressure (12 bar) for 20 h. After the reaction has ended, isooctane (internal standard) and 10 ml of EtOAc are added. The organic phase was analysed by GC.

Scheme 23: MINO synthesis

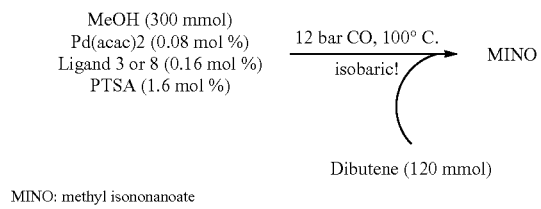

MINO: methyl isononanoate

Figure 12:
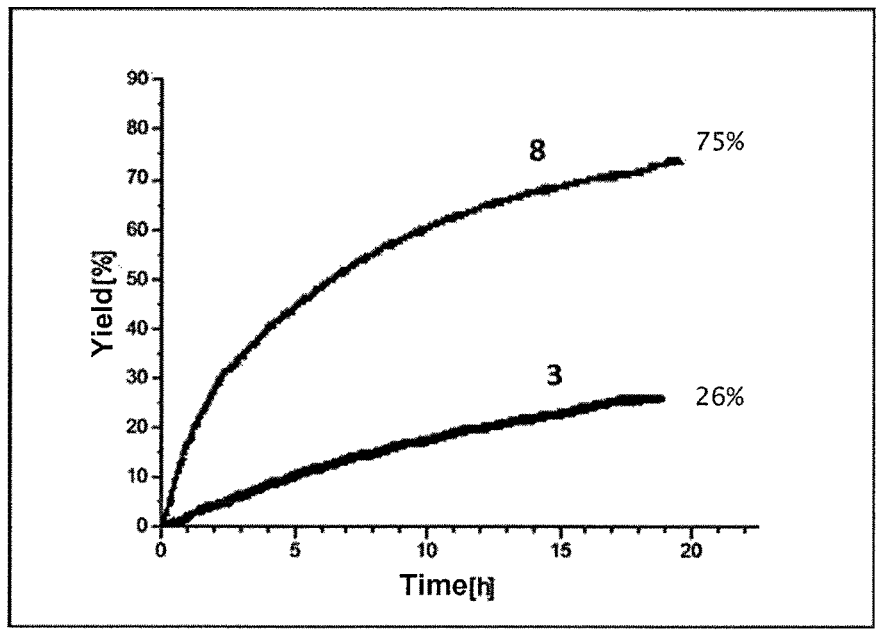
FIG. 12 gas consumption curves of reactions with 3 and 8.

The results are shown in FIG. 12.

FIG. 12: Gas consumption curves of reactions with 3 and 8.

C-18 Olefins

Methyl oleate (Alfa Aesar, H311358, LOT:10164632)

Conversion of Methyl Oleate with Ligands 3 and 8

Scheme 24: Conversion of methyl oleate with ligands 3 and 8

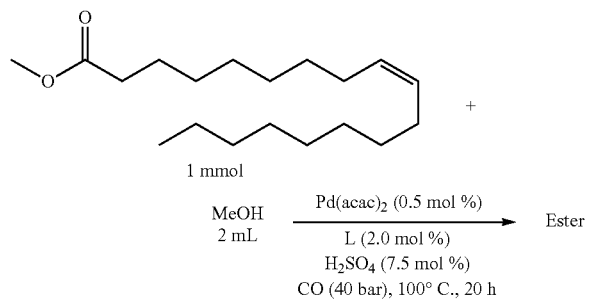

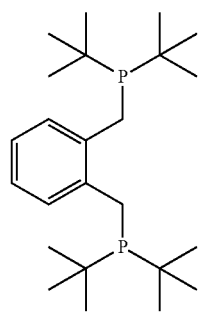

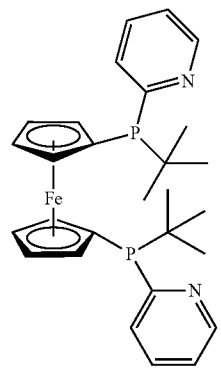

3 (comparative example): A 25 ml Schlenk vessel was charged with [Pd(acac)$_2$] (4.57 mg, 0.05 mol %), H$_2$SO$_4$ (22.05 mg, 7.5 mol %) and MeOH (6 ml). A 4 ml vial was charged with 3 (7.9 mg, 2.0 mol %), and a magnetic stirrer bar was added. Thereafter, 2 ml of the clear yellow solution and methyl oleate (339 μl, 1 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (100 μl) was added as internal GC standard. Yield and regioselectivity were determined by means of GC. Yield of linear ester: 54%, no branched ester.

8: A 25 ml Schlenk vessel was charged with [Pd(acac)$_2$] (4.57 mg, 0.05 mol %), H$_2$SO$_4$ (22.05 mg, 7.5 mol %) and MeOH (6 ml). A 4 ml vial was charged with 8 (10.3 mg, 2.0 mol %), and a magnetic stirrer bar was added. Thereafter, 2 ml of the clear yellow solution and methyl oleate (339 μl, 1 mmol) were added with a syringe. The vial was placed into a sample holder which was in turn inserted into a 300 ml Parr autoclave under an argon atmosphere. After the autoclave had been purged three times with nitrogen, the CO pressure was adjusted to 40 bar. The reaction proceeded at 100° C. for 20 hours. On conclusion of the reaction, the autoclave was cooled down to room temperature and cautiously decompressed. Isooctane (100 μl) was added as internal GC standard. Yield and regioselectivity were determined by means of GC. Yield of linear ester: 98%, no branched ester.

It is apparent from the results that the inventive ligand 8 is better suited to conversion of methyl oleate than ligand 3 from the prior art.

Conversion of Various Olefins Under Optimized Conditions

The conditions of the methoxycarbonylation of di-n-butene were optimized as follows:

Scheme 25: Optimized conditions

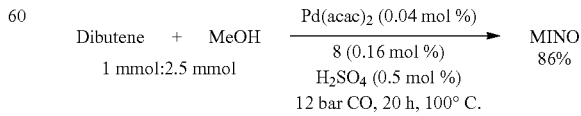

The optimized conditions were applied to a series of alkenes (Table 1).

Scheme 26: Optimized conditions with various reactants

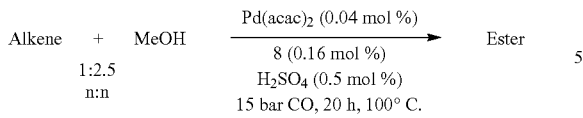

Method: Baked-out glass vials were each initially charged with 1 mg (0.04 mol %) of Pd(acac)$_2$ and 7.2 mg (0.16 mol %) of ligand 8, and 812 µl (20 mmol) of methanol (technical grade) and 8 mmol of alkene in each case were added. Then 2 µl (0.5 mol %) of H$_2$SO$_4$ (98%) (100 µl of a sulphuric acid solution in methanol contain 2 µl of sulphuric acid) are added.

The reactions in the autoclave are purged twice with CO at 10 bar, charged with CO to 15 bar and stirred at 100° C. for 20 h. After the reaction has ended, isooctane (internal standard) and 1 ml of EtOAc are added in each case. The organic phase is analysed by GC.

The results are compiled in Table 1.

TABLE 1

Substrate testing with various alkenes

| Alkene | Alkene [%] | Ester [%] | n-Selectivity [%] |
|---|---|---|---|
| Di-n-butene | 16 | 82 | 79 |
| 1-Octene | 0 | 100 | 72 |
| 1-Decene | 0 | 100 | 72 |
| 1-Hexene | 0 | 100 | 78 |
| 2-Octene | 2 | 98 | 72 |
| Limonene | 27 | 14 | — |
| Vinylcyclohexene | 13 | 52 | 95 |
| 1,7-Octadiene | 27 | 26 | 65 |
| Methyl 10-undecanoate | 13 | 86 | 75 |
| Methyl oleate | 23 | 75 | not attributable |
| Methyl 3-pentenoate | 23 | 74 | 82 |

The n selectivity in Table 1 is defined as the proportion of terminal methoxycarbonylation based on the overall yield of the methoxycarbonylation products.

It is found that linear terminal olefins such as 1-octene, 1-decene, 1-hexene and 2-octene give quantitative ester yields. Good yields are likewise afforded by methyl 3-pentenoate, methyl oleate and methyl undecenoate. In the case of vinylcyclohexene, there is 52% monomethoxycarbonylation and also partial methoxycarbonylation of the internal double bond (35%). Octadiene is singly methoxycarbonylated to an extent of 55% and doubly methoxycarbonylated to an extent of 26%.

The experiments described show that the compounds according to the invention are suitable as catalyst ligands for the alkoxycarbonylation of a multitude of ethylenically unsaturated compounds. More particularly, with the compounds according to the invention, better yields are achieved than with the bidentate phosphine ligands known from the prior art, such as 1,2-bis(di-tert-butylphosphinomethyl)benzene (DTBPMB, ligand 3), 1,1'-bis(diphenylphosphino)ferrocene (ligand 59), 1-(diphenylphosphino)-1'-(diisopropylphosphino)ferrocene (ligand 10) and 1,1'-bis(isopropylphenylphosphino)ferrocene (ligand 19). In addition, the compounds according to the invention also enable the alkoxycarbonylation of long-chain olefins of industrial importance, such as di-n-butene and 2-octene, and also of olefin mixtures such as the raffinate 1 described.

The invention claimed is:

1. Compound of formula (I)

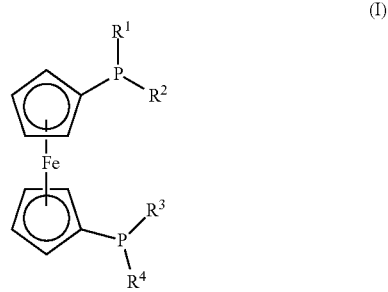

where
R$^1$, R$^2$, R$^3$, R$^4$ are each independently selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, —(C$_3$-C$_{20}$)-heteroaryl;
at least one of the R$^1$, R$^2$, R$^3$, R$^4$ radicals is a —(C$_6$-C$_{20}$)-heteroaryl radical having at least six ring atoms; and
R$^1$, R$^2$, R$^3$, R$^4$, if they are —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, —(C$_3$-C$_{20}$)-heteroaryl or —(C$_6$-C$_{20}$)-heteroaryl, may each independently be substituted by one or more substituents selected from —(C$_1$-C$_{12}$)-alkyl, —(C$_3$-C$_{12}$)-cycloalkyl, —(C$_3$-C$_{12}$)-heterocycloalkyl, —O—(C$_1$-C$_2$)-alkyl, —O—(C$_1$-C$_{12}$)-alkyl-(C$_6$-C$_{20}$)-aryl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —CO—(C$_1$-C$_{12}$)-alkyl, —CO—(C$_3$-C$_{12}$)-cycloalkyl, —N—[(C$_1$-C$_{12}$)-alkyl]$_2$, —(C$_6$-C$_{20}$)-aryl, —(C$_6$-C$_{20}$)-aryl-(C$_1$-C$_{12}$)-alkyl, —(C$_6$-C$_{20}$)-aryl-O—(C$_1$-C$_{12}$)-alkyl, —(C$_3$-C$_{20}$)-heteroaryl, —(C$_3$-C$_{20}$)-heteroaryl-(C$_1$-C$_{12}$)-alkyl, —(C$_3$-C$_{20}$)-heteroaryl-O—(C$_1$-C$_{12}$)-alkyl, —COOH, —OH, —SO$_3$H, —NH$_2$, halogen.

2. Compound according to claim 1,
where at least two of the R$^1$, R$^2$, R$^3$, R$^4$ radicals are a —(C$_6$-C$_{20}$)-heteroaryl radical having at least six ring atoms.

3. Compound according to claim 1,
where the R$^1$ and R$^3$ radicals are each a —(C$_6$-C$_{20}$)-heteroaryl radical having at least six ring atoms.

4. Compound according to claim 1,
where the R$^1$ and R$^3$ radicals are each a —(C$_6$-C$_{20}$)-heteroaryl radical having at least six ring atoms;
R$^2$ is —(C$_6$-C$_{20}$)-heteroaryl having at least six ring atoms or is selected from —(C$_1$-C$_{12}$)-alkyl, —(C$_3$-C$_{12}$)-cycloalkyl, —(C$_3$-C$_2$)-heterocycloalkyl, —(C$_6$-C$_{20}$)-aryl;
and R$^4$ is selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl.

5. Compound according to claim 1,
where the R$^1$ and R$^3$ radicals are each a —(C$_6$-C$_{20}$)-heteroaryl radical having at least six ring atoms;
and R$^2$ and R$^4$ are selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl.

6. Compound according to claim 1,
where the R$^1$ and R$^3$ radicals are each a —(C$_6$-C$_{20}$)-heteroaryl radical having at least six ring atoms;
and R$^2$ and R$^4$ are —(C$_1$-C$_{12}$)-alkyl.

7. Compound according to claim 1,
where $R^1$, $R^2$, $R^3$, $R^4$, if they are a heteroaryl radical, are each independently selected from pyridyl, pyridazinyl, pyrimidyl, pyrazinyl, benzofuranyl, indolyl, isoindolyl, benzimidazolyl, quinolyl, isoquinolyl.

8. Compound according to claim 1,
of one of the formulae (8), (14) and (15)

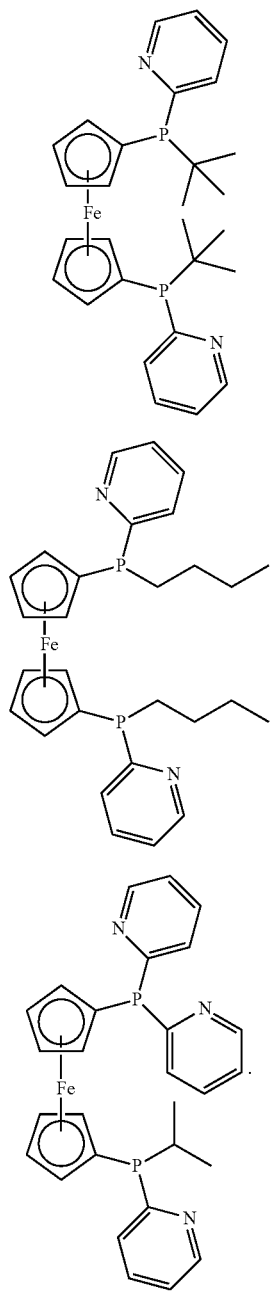

9. Complex comprising Pd and a compound according to claim 1.

10. Process comprising the following process steps:
a) initially charging an ethylenically unsaturated compound;
b) adding a compound of formula (I)

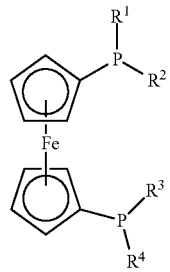

where
$R^1$, $R^2$, $R^3$, $R^4$ are each independently selected from —$(C_1-C_{12})$-alkyl, —$(C_3-C_{12})$-cycloalkyl, —$(C_3-C_2)$-heterocycloalkyl, —$(C_6-C_{20})$-aryl, —$(C_3-C_{20})$-heteroaryl;
at least one of the $R^1$, $R^2$, $R^3$, $R^4$ radicals is a —$(C_6-C_{20})$-heteroaryl radical having at least six ring atoms;
and
$R^1$, $R^2$, $R^3$, $R^4$, if they are —$(C_1-C_{12})$-alkyl, —$(C_3-C_{12})$-cycloalkyl, —$(C_3-C_{12})$-heterocycloalkyl, —$(C_6-C_{20})$-aryl, —$(C_3-C_{20})$-heteroaryl or —$(C_6-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —COO—$(C_1-C_{12})$-alkyl, —COO—$(C_3-C_2)$-cycloalkyl, —CONH—$(C_1-C_{12})$-alkyl, —CONH—$(C_3-C_{12})$-cycloalkyl, —CO—$(C_1-C_{12})$-alkyl, —CO—$(C_3-C_{12})$-cycloalkyl, —N—$[(C_1-C_{12})$-alkyl]$_2$, —$(C_6-C_{20})$-aryl, —$(C_6-C_{20})$-aryl-$(C_1-C_{12})$-alkyl, —$(C_6-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —$SO_3H$, —$NH_2$, halogen and a compound comprising Pd,
or adding a complex according to claim 9;
c) adding an alcohol;
d) feeding in CO;
e) heating the reaction mixture, with conversion of the ethylenically unsaturated compound to an ester.

11. Process according to claim 10,
wherein the ethylenically unsaturated compound is selected from ethene, propene, 1-butene, cis- and/or trans-2-butene, isobutene, 1,3-butadiene, l-pentene, cis- and/or trans-2-pentene, 2-methyl-1-butene, 3-methyl-1-butene, 2-methyl-2-butene, hexene, tetramethylethylene, heptene, l-octene, 2-octene, di-n-butene, and mixtures thereof.

12. Process according to claim 10,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone) palladium, bis(acetonitrile)dichloropalladium(II), palladium(cinnamyl) dichloride.

13. Process according to claim 10,
wherein the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

14. A process for preparing an alkoxycarbonylation reaction medium, comprising preparing the medium by introducing to a medium, a compound of formula (I)

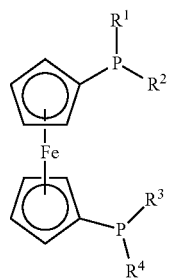

(I)

where
$R^1$, $R^2$, $R^3$, $R^4$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl;

at least one of the $R^1$, $R^2$, $R^3$, $R^4$ radicals is a —$(C_6$-$C_{20})$-heteroaryl radical having at least six ring atoms; and $R^1$, $R^2$, $R^3$, $R^4$, if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl or —$(C_6$-$C_{20})$-heteroaryl, may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_2)$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —SO$_3$H, —NH$_2$, halogen or a complex according to claim 9.

15. The compound of claim 1, wherein $R^1$, $R^2$, $R^3$, $R^4$ are each independently selected from —$(C_1$-$C_8)$-alkyl, —$(C_3$-$C_8)$-cycloalkyl, —$(C_3$-$C_8)$-heterocycloalkyl, —$(C_6$-$C_{14})$-aryl, or —$(C_6$-$C_{14})$-heteroaryl.

16. The compound of claim 1, wherein at least one of the $R^1$, $R^2$, $R^3$, $R^4$ radicals is a —$(C_6$-$C_{14})$-heteroaryl radical having at least six ring atoms.

* * * * *